US010314649B2

(12) United States Patent
Bakos et al.

(10) Patent No.: US 10,314,649 B2
(45) Date of Patent: Jun. 11, 2019

(54) FLEXIBLE EXPANDABLE ELECTRODE AND METHOD OF INTRALUMINAL DELIVERY OF PULSED POWER

(75) Inventors: Gregory J. Bakos, Mason, OH (US); David N. Plescia, Mentor, OH (US); Gary L. Long, Cincinnati, OH (US); Peter K. Shires, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 847 days.

(21) Appl. No.: 13/565,307

(22) Filed: Aug. 2, 2012

(65) Prior Publication Data

US 2014/0039491 A1 Feb. 6, 2014

(51) Int. Cl.
*A61B 18/18* (2006.01)
*A61B 18/14* (2006.01)
(Continued)

(52) U.S. Cl.
CPC ............ *A61B 18/1492* (2013.01); *A61B 2017/00867* (2013.01); *A61B 2018/00196* (2013.01);
(Continued)

(58) Field of Classification Search
CPC . A61N 1/05; A61N 1/08; A61N 1/375; A61N 2/02; A61N 1/0058; A61N 1/057;
(Continued)

(56) References Cited

U.S. PATENT DOCUMENTS

| 112,794 A | 3/1871 | Felton |
| 645,576 A | 3/1900 | Tesla |
| (Continued) | | |

FOREIGN PATENT DOCUMENTS

| AU | 666310 B2 | 2/1996 |
| DE | 3008120 A1 | 9/1980 |
| (Continued) | | |

OTHER PUBLICATIONS

International Search Report for PCT/US2013/052250, dated Oct. 29, 2013 (7 pages).
(Continued)

*Primary Examiner* — Christopher Koharski
*Assistant Examiner* — Elizabeth K So

(57) ABSTRACT

A surgical instrument, such as an electrical ablation device, includes an elongate member having therealong disposed a first electrode extending along an axis. A first expandable portion extends along the axis and defines a first perimeter of the first electrode and has an associated first diameter with respect to the axis. The first expandable portion includes a first framework selectively expandable to transition the first expandable portion from a contracted state to an expanded state. The first framework is selectively contractible to transition the first expandable portion from the expanded state to the contracted state. When the first framework is expanded, the first diameter is expanded and the first expandable portion is transitioned from the contracted state to the expanded state. When the first framework is contracted, the first diameter is contracted and the first expandable portion is transitioned from the expanded state to the contracted state.

15 Claims, 16 Drawing Sheets

(51) Int. Cl.
    *A61B 17/00*     (2006.01)
    *A61B 18/00*     (2006.01)

(52) U.S. Cl.
    CPC ............ *A61B 2018/00202* (2013.01); *A61B 2018/00267* (2013.01); *A61B 2018/00357* (2013.01); *A61B 2018/00577* (2013.01); *A61B 2018/00613* (2013.01); *A61B 2018/1435* (2013.01); *A61B 2018/1465* (2013.01); *A61B 2018/1475* (2013.01)

(58) Field of Classification Search
    CPC ...... A61N 1/0573; A61N 1/059; A61B 18/18; A61B 18/1492; A61B 2018/0053; A61B 2018/0016; A61B 2018/00184; A61B 2018/00202; A61B 2018/00267; A61B 2018/00273; A61B 2018/00279; A61B 2018/00952; A61B 2018/00357; A61B 2018/00613; A61B 2018/00577; A61B 2018/1465; A61B 2018/00196; A61B 2017/00867; A61B 2018/1475; A61B 2018/1435; A61F 2/82; A61F 2/844; A61F 2/86

See application file for complete search history.

(56) References Cited

U.S. PATENT DOCUMENTS

| | | |
|---|---|---|
| 649,621 A | 5/1900 | Tesla |
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |
| 1,581,706 A | 4/1926 | White |
| 1,581,707 A | 4/1926 | White |
| 1,581,708 A | 4/1926 | White |
| 1,581,709 A | 4/1926 | White |
| 1,581,710 A | 4/1926 | White |
| 1,625,602 A | 4/1927 | Gould et al. |
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,137,710 A | 11/1938 | Anderson |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,451,077 A | 10/1948 | Emsig |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,110,956 A | 11/1963 | Fischer, Jr. |
| 3,170,471 A | 2/1965 | Schnitzer |
| 3,435,824 A | 4/1969 | Gamponia |
| 3,470,876 A | 10/1969 | Barchilon |
| 3,481,325 A | 12/1969 | Glassman |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,854,743 A | 12/1974 | Hansen |
| 3,929,123 A | 12/1975 | Jamshidi |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,043,342 A | 8/1977 | Morrison, Jr. |
| 4,071,028 A | 1/1978 | Perkins |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,393,872 A | 7/1983 | Reznik et al. |
| 4,396,021 A | 8/1983 | Baumgartner |
| 4,396,139 A | 8/1983 | Hall et al. |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,492,232 A | 1/1985 | Green |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,649,904 A | 3/1987 | Krauter et al. |
| 4,653,476 A | 3/1987 | Bonnet |
| 4,655,219 A | 4/1987 | Petruzzi |
| 4,657,016 A | 4/1987 | Garito et al. |
| 4,657,018 A | 4/1987 | Hakky |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,239 A | 12/1987 | Sorochenko et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,742,817 A | 5/1988 | Kawashima et al. |
| 4,753,223 A | 6/1988 | Bremer |
| 4,763,669 A | 8/1988 | Jaeger |
| 4,770,188 A | 9/1988 | Chikama |
| 4,790,624 A | 12/1988 | Van Hoye et al. |
| 4,791,707 A | 12/1988 | Tucker |
| 4,796,627 A | 1/1989 | Tucker |
| 4,807,593 A | 2/1989 | Ito |
| 4,815,450 A | 3/1989 | Patel |
| 4,819,620 A | 4/1989 | Okutsu |
| 4,823,794 A | 4/1989 | Pierce |
| 4,829,999 A | 5/1989 | Auth |
| 4,836,188 A | 6/1989 | Berry |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,904,048 A | 2/1990 | Sogawa et al. |
| 4,911,148 A | 3/1990 | Sosnowski et al. |
| 4,926,860 A | 5/1990 | Stice et al. |
| 4,934,364 A | 6/1990 | Green |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,496 A | 12/1990 | Komi |
| 4,979,950 A | 12/1990 | Transue et al. |

(56) References Cited

U.S. PATENT DOCUMENTS

| | | |
|---|---|---|
| 4,984,581 A | 1/1991 | Stice |
| 4,990,152 A | 2/1991 | Yoon |
| 4,991,565 A | 2/1991 | Takahashi et al. |
| 4,994,079 A | 2/1991 | Genese et al. |
| 5,007,917 A | 4/1991 | Evans |
| 5,010,876 A | 4/1991 | Henley et al. |
| 5,015,249 A | 5/1991 | Nakao et al. |
| 5,020,514 A | 6/1991 | Heckele |
| 5,020,535 A | 6/1991 | Parker et al. |
| 5,025,778 A | 6/1991 | Silverstein et al. |
| 5,026,379 A | 6/1991 | Yoon |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,049,153 A | 9/1991 | Nakao et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,098,378 A | 3/1992 | Piontek et al. |
| 5,099,827 A | 3/1992 | Melzer et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,156,609 A | 10/1992 | Nakao et al. |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,961 A | 6/1993 | Nakao et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,336,192 A | 8/1994 | Palestrant |
| 5,336,222 A | 8/1994 | Durgin, Jr. et al. |
| 5,339,805 A | 8/1994 | Parker |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,348,259 A | 9/1994 | Blanco et al. |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,368,606 A | 11/1994 | Marlow et al. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,374,953 A | 12/1994 | Sasaki et al. |
| 5,376,077 A | 12/1994 | Gomringer |
| 5,377,695 A | 1/1995 | An Haack |
| 5,378,234 A | 1/1995 | Hammerslag et al. |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,367 A | 3/1995 | Wilk |
| 5,395,381 A | 3/1995 | Green et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,326 A | 4/1995 | Harrison et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |
| 5,433,735 A | 7/1995 | Zanakis et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |

(56) References Cited

U.S. PATENT DOCUMENTS

| | | |
|---|---|---|
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,472,441 A | 12/1995 | Edwards et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,499,997 A | 3/1996 | Sharpe et al. |
| 5,500,012 A | 3/1996 | Brucker et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,234 A | 7/1996 | Newman |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |
| 5,607,386 A | 3/1997 | Flam |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkier et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,519 A | 7/1997 | Lee et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,276 A | 10/1997 | Lundquist |
| 5,681,279 A | 10/1997 | Roper et al. |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,759,150 A | 6/1998 | Konou et al. |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |

(56) References Cited

U.S. PATENT DOCUMENTS

| | | |
|---|---|---|
| 5,797,960 A | 8/1998 | Stevens et al. |
| 5,800,449 A | 9/1998 | Wales |
| 5,800,451 A | 9/1998 | Buess et al. |
| 5,803,903 A | 9/1998 | Athas et al. |
| 5,807,395 A | 9/1998 | Mulier et al. |
| 5,808,665 A | 9/1998 | Green |
| 5,810,805 A | 9/1998 | Sutcu et al. |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |
| 5,836,960 A | 11/1998 | Kolesa et al. |
| 5,843,017 A | 12/1998 | Yoon |
| 5,843,097 A | 12/1998 | Mayenberger et al. |
| 5,843,121 A | 12/1998 | Yoon |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,873,849 A | 2/1999 | Bernard |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,919,207 A | 7/1999 | Taheri |
| 5,921,892 A | 7/1999 | Easton |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A | 8/1999 | Hahnen |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,933 A | 11/1999 | Yoon |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,033,401 A | 3/2000 | Edwards et al. |
| 6,036,640 A | 3/2000 | Corace et al. |
| 6,036,685 A | 3/2000 | Mueller |
| 6,050,992 A | 4/2000 | Nichols |
| 6,053,927 A | 4/2000 | Hamas |
| 6,053,937 A | 4/2000 | Edwards et al. |
| 6,059,719 A | 5/2000 | Yamamoto et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,086,600 A | 7/2000 | Kortenbach |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,718 A | 9/2000 | Tu et al. |
| 6,131,790 A | 10/2000 | Piraka |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,871 A | 11/2000 | Foley et al. |
| 6,152,920 A | 11/2000 | Thompson et al. |

(56) References Cited

U.S. PATENT DOCUMENTS

| | | |
|---|---|---|
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,173,872 B1 | 1/2001 | Cohen |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,248,124 B1 | 6/2001 | Pedros et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,287,304 B1 | 9/2001 | Eggers et al. |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,269 B1 | 2/2002 | Shipp et al. |
| 6,350,278 B1 | 2/2002 | Lenker et al. |
| 6,352,503 B1 | 3/2002 | Matsui et al. |
| 6,352,541 B1 | 3/2002 | Kienzle et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,444 B1 | 9/2002 | Avni et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,074 B1 | 10/2002 | Matsui et al. |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,517,534 B1 | 2/2003 | McGovern et al. |
| 6,520,954 B2 | 2/2003 | Ouchi |
| 6,526,320 B2 | 2/2003 | Mitchell |
| 6,527,753 B2 | 3/2003 | Sekine et al. |
| 6,527,782 B2 | 3/2003 | Hogg et al. |
| 6,530,880 B2 | 3/2003 | Pagliuca |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,551,356 B2 | 4/2003 | Rousseau |
| 6,554,766 B2 | 4/2003 | Maeda et al. |
| 6,554,823 B2 | 4/2003 | Palmer et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,120 B1 | 5/2003 | Green et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,594,971 B1 | 7/2003 | Addy et al. |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,171 B2 | 10/2003 | Iddan et al. |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,545 B2 | 11/2003 | Shipp et al. |
| 6,652,551 B1 | 11/2003 | Heiss |
| 6,656,194 B1 | 12/2003 | Gannoe et al. |

(56) References Cited

U.S. PATENT DOCUMENTS

| | | |
|---|---|---|
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,070 B2 | 1/2004 | Edwards et al. |
| 6,673,087 B1 | 1/2004 | Chang et al. |
| 6,673,092 B1 | 1/2004 | Bacher |
| 6,676,685 B2 | 1/2004 | Pedros et al. |
| 6,679,882 B1 | 1/2004 | Kornerup |
| 6,684,938 B2 | 2/2004 | Tsujita et al. |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,695,867 B2 | 2/2004 | Ginn et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,740,082 B2 | 5/2004 | Shadduck |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,767,356 B2 | 7/2004 | Kanner et al. |
| 6,773,434 B2 | 8/2004 | Ciarrocca |
| 6,776,165 B2 | 8/2004 | Jin |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,821,285 B2 | 11/2004 | Laufer et al. |
| 6,824,548 B2 | 11/2004 | Smith et al. |
| 6,830,545 B2 | 12/2004 | Bendall |
| 6,835,200 B2 | 12/2004 | Laufer et al. |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |
| 6,939,347 B2 | 9/2005 | Thompson |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,955,641 B2 | 10/2005 | Lubock |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,960,183 B2 | 11/2005 | Nicolette |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,738 B2 | 1/2006 | Glukhovsky et al. |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,602 B2 | 1/2006 | Nakazawa et al. |
| 6,991,627 B2 | 1/2006 | Madhani et al. |
| 6,991,631 B2 | 1/2006 | Woloszko et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,011,669 B2 | 3/2006 | Kimblad |
| 7,018,373 B2 | 3/2006 | Suzuki |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |

(56) References Cited

U.S. PATENT DOCUMENTS

| | | |
|---|---|---|
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,559 B2 | 7/2006 | Adams et al. |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,010 B2 | 8/2006 | Ootawara et al. |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,115,785 B2 | 10/2006 | Guggenheim et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,122,605 B2 | 10/2006 | Ohrbom et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,156,845 B2 | 1/2007 | Mulier et al. |
| 7,160,296 B2 | 1/2007 | Pearson et al. |
| 7,163,525 B2 | 1/2007 | Franer |
| 7,169,104 B2 | 1/2007 | Ueda et al. |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,186,265 B2 | 3/2007 | Sharkawy et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,204,840 B2 | 4/2007 | Skakoon et al. |
| 7,207,997 B2 | 4/2007 | Shipp et al. |
| 7,208,005 B2 | 4/2007 | Frecker et al. |
| 7,211,089 B2 | 5/2007 | Kear et al. |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francere et al. |
| 7,226,458 B2 | 6/2007 | Kaplan et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,084 B2 | 6/2007 | Skakoon et al. |
| 7,235,089 B1 | 6/2007 | McGuckin, Jr. |
| 7,241,290 B2 | 7/2007 | Doyle et al. |
| 7,241,295 B2 | 7/2007 | Maguire |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,288,075 B2 | 10/2007 | Parihar et al. |
| 7,290,615 B2 | 11/2007 | Christanti et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,341,554 B2 | 3/2008 | Sekine et al. |
| 7,344,536 B1 | 3/2008 | Lunsford et al. |
| 7,349,223 B2 | 3/2008 | Haemer et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,442,166 B2 | 10/2008 | Huang et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,514,568 B2 | 4/2009 | Freeman |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,535,570 B2 | 5/2009 | Muraishi |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |

(56) References Cited

U.S. PATENT DOCUMENTS

| | | |
|---|---|---|
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,005 B2 | 8/2009 | Keeler et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,591,781 B2 | 9/2009 | Hirata |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,612,084 B2 | 11/2009 | James et al. |
| 7,615,002 B2 | 11/2009 | Rothweiler et al. |
| 7,615,005 B2 | 11/2009 | Stefanchik et al. |
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,282 B2 | 3/2010 | Mathis |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,684,851 B2 | 3/2010 | Miyake et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,710,563 B2 | 5/2010 | Betzig et al. |
| 7,713,189 B2 | 5/2010 | Hanke |
| 7,713,270 B2 | 5/2010 | Suzuki |
| 7,721,742 B2 | 5/2010 | Kalloo et al. |
| 7,722,631 B2 | 5/2010 | Mikkaichi et al. |
| 7,736,374 B2 | 6/2010 | Vaughan et al. |
| 7,744,613 B2 | 6/2010 | Ewers et al. |
| 7,744,615 B2 | 6/2010 | Couture |
| 7,749,161 B2 | 7/2010 | Beckman et al. |
| 7,751,866 B2 | 7/2010 | Aoki et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,766,896 B2 | 8/2010 | Kornkven Volk et al. |
| 7,770,584 B2 | 8/2010 | Danek et al. |
| 7,771,416 B2 | 8/2010 | Spivey et al. |
| 7,771,437 B2 | 8/2010 | Hogg et al. |
| 7,776,035 B2 | 8/2010 | Rick et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,447 B2 | 9/2010 | Dann et al. |
| 7,794,458 B2 | 9/2010 | McIntyre et al. |
| 7,794,475 B2 | 9/2010 | Hess et al. |
| 7,798,386 B2 | 9/2010 | Schall et al. |
| 7,798,750 B2 | 9/2010 | Clark |
| 7,815,565 B2 | 10/2010 | Stefanchik et al. |
| 7,815,566 B2 | 10/2010 | Stefanchik et al. |
| 7,815,651 B2 | 10/2010 | Skakoon et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,828,186 B2 | 11/2010 | Wales |
| 7,828,809 B2 | 11/2010 | Skakoon et al. |
| 7,833,156 B2 | 11/2010 | Williams et al. |
| 7,833,231 B2 | 11/2010 | Skakoon et al. |
| 7,833,238 B2 | 11/2010 | Nakao |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,857,820 B2 | 12/2010 | Skakoon et al. |
| 7,862,546 B2 | 1/2011 | Conlon et al. |
| 7,862,553 B2 | 1/2011 | Ewaschuk |
| 7,867,216 B2 | 1/2011 | Wahr et al. |
| 7,871,371 B2 | 1/2011 | Komiya et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,558 B2 | 2/2011 | Lin et al. |
| 7,892,200 B2 | 2/2011 | Birk et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,916,809 B2 | 3/2011 | Tsushima |
| 7,918,785 B2 | 4/2011 | Okada et al. |
| 7,918,869 B2 | 4/2011 | Saadat et al. |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,937,143 B2 | 5/2011 | Demarais et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,959,627 B2 | 6/2011 | Utley et al. |
| 7,959,629 B2 | 6/2011 | Young et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,458 B2 | 7/2011 | Stefanchik et al. |
| 7,976,552 B2 | 7/2011 | Suzuki |
| 7,985,239 B2 | 7/2011 | Suzuki |
| 7,985,830 B2 | 7/2011 | Mance et al. |
| 7,988,618 B2 | 8/2011 | Mikkaichi et al. |
| 7,988,685 B2 | 8/2011 | Ziaie et al. |
| 8,007,495 B2 | 8/2011 | McDaniel et al. |
| 8,021,362 B2 | 9/2011 | Deem et al. |
| 8,029,504 B2 | 10/2011 | Long |
| 8,034,046 B2 | 10/2011 | Eidenschink |
| 8,037,591 B2 | 10/2011 | Spivey et al. |
| 8,043,289 B2 | 10/2011 | Behl et al. |
| 8,048,067 B2 | 11/2011 | Davalos et al. |
| 8,048,108 B2 | 11/2011 | Sibbitt et al. |
| 8,052,699 B1 | 11/2011 | Sherwinter |
| 8,057,510 B2 | 11/2011 | Ginn et al. |
| 8,062,306 B2 | 11/2011 | Nobis et al. |
| 8,062,311 B2 | 11/2011 | Litscher et al. |
| 8,066,632 B2 | 11/2011 | Dario et al. |
| 8,066,702 B2 | 11/2011 | Rittman, III et al. |
| 8,070,759 B2 | 12/2011 | Stefanchik et al. |
| 8,070,804 B2 | 12/2011 | Hyde et al. |
| 8,075,572 B2 | 12/2011 | Stefanchik et al. |

(56) References Cited

U.S. PATENT DOCUMENTS

| | | |
|---|---|---|
| 8,075,587 B2 | 12/2011 | Ginn |
| 8,083,787 B2 | 12/2011 | Korb et al. |
| 8,088,062 B2 | 1/2012 | Zwolinski |
| 8,096,459 B2 | 1/2012 | Ortiz et al. |
| 8,096,941 B2 | 1/2012 | Fowler et al. |
| 8,100,922 B2 | 1/2012 | Griffith |
| 8,105,342 B2 | 1/2012 | Onuki et al. |
| 8,109,872 B2 | 2/2012 | Kennedy, II et al. |
| 8,114,072 B2 | 2/2012 | Long et al. |
| 8,114,119 B2 | 2/2012 | Spivey et al. |
| 8,115,447 B2 | 2/2012 | Toya et al. |
| 8,118,821 B2 | 2/2012 | Mouw |
| 8,118,834 B1 | 2/2012 | Goraltchouk et al. |
| 8,131,371 B2 | 3/2012 | Demarals et al. |
| 8,147,424 B2 | 4/2012 | Kassab et al. |
| 8,157,813 B2 | 4/2012 | Ko et al. |
| 8,157,834 B2 | 4/2012 | Conlon |
| 8,172,772 B2 | 5/2012 | Zwolinski et al. |
| 8,182,414 B2 | 5/2012 | Handa et al. |
| 8,187,166 B2 | 5/2012 | Kuth et al. |
| 8,200,334 B1 | 6/2012 | Min et al. |
| 8,206,295 B2 | 6/2012 | Kaul |
| 8,211,125 B2 | 7/2012 | Spivey |
| 8,216,224 B2 | 7/2012 | Morris et al. |
| 8,221,310 B2 | 7/2012 | Saadat et al. |
| 8,221,411 B2 | 7/2012 | Francischelli et al. |
| 8,222,385 B2 | 7/2012 | Yoshizaki et al. |
| 8,241,204 B2 | 8/2012 | Spivey |
| 8,251,068 B2 | 8/2012 | Schnell |
| 8,252,057 B2 | 8/2012 | Fox |
| 8,262,563 B2 | 9/2012 | Bakos et al. |
| 8,262,655 B2 | 9/2012 | Ghabrial et al. |
| 8,262,680 B2 | 9/2012 | Swain et al. |
| 8,267,854 B2 | 9/2012 | Asada et al. |
| 8,303,581 B2 | 11/2012 | Arts et al. |
| 8,308,738 B2 | 11/2012 | Nobis et al. |
| 8,317,806 B2 | 11/2012 | Coe et al. |
| 8,317,814 B2 | 11/2012 | Karasawa et al. |
| 8,328,836 B2 | 12/2012 | Conlon et al. |
| 8,337,394 B2 | 12/2012 | Vakharia |
| 8,337,492 B2 | 12/2012 | Kunis et al. |
| 8,343,041 B2 | 1/2013 | Byers et al. |
| 8,353,487 B2 | 1/2013 | Trusty et al. |
| 8,357,170 B2 | 1/2013 | Stefanchik |
| 8,359,093 B2 | 1/2013 | Wariar |
| 8,361,066 B2 | 1/2013 | Long et al. |
| 8,361,112 B2 | 1/2013 | Carroll, II et al. |
| 8,366,733 B2 | 2/2013 | Gabel et al. |
| 8,377,057 B2 | 2/2013 | Rick et al. |
| 8,403,926 B2 | 3/2013 | Nobis et al. |
| 8,409,200 B2 | 4/2013 | Holcomb et al. |
| 8,425,505 B2 | 4/2013 | Long |
| 8,430,811 B2 | 4/2013 | Hess et al. |
| 8,449,452 B2 | 5/2013 | Iddan et al. |
| 8,449,538 B2 | 5/2013 | Long |
| 8,454,594 B2 * | 6/2013 | Demarais .............. A61N 1/32 606/41 |
| 8,475,359 B2 | 7/2013 | Asada et al. |
| 8,475,452 B2 | 7/2013 | Van Wyk et al. |
| 8,480,657 B2 | 7/2013 | Bakos |
| 8,480,689 B2 | 7/2013 | Spivey et al. |
| 8,485,968 B2 | 7/2013 | Weimer et al. |
| 8,496,574 B2 | 7/2013 | Trusty et al. |
| 8,500,697 B2 | 8/2013 | Kurth et al. |
| 8,506,564 B2 | 8/2013 | Long et al. |
| 8,512,335 B2 | 8/2013 | Cheng et al. |
| 8,523,884 B2 | 9/2013 | Stam et al. |
| 8,523,939 B1 | 9/2013 | Hausen |
| 8,529,563 B2 | 9/2013 | Long et al. |
| 8,545,396 B2 | 10/2013 | Cover et al. |
| 8,568,410 B2 | 10/2013 | Vakharia et al. |
| 8,579,897 B2 | 11/2013 | Vakharia et al. |
| 8,608,652 B2 | 12/2013 | Voegele et al. |
| 8,623,011 B2 | 1/2014 | Spivey |
| 8,636,648 B2 | 1/2014 | Gazdzinski |
| 8,636,730 B2 | 1/2014 | Keppel |
| 8,640,940 B2 | 2/2014 | Ohdaira |
| 8,652,150 B2 | 2/2014 | Swain et al. |
| 8,668,686 B2 | 3/2014 | Govari et al. |
| 8,679,003 B2 | 3/2014 | Spivey |
| 8,685,058 B2 | 4/2014 | Wilk |
| 8,727,967 B2 | 5/2014 | Weitzner |
| 8,747,401 B2 | 6/2014 | Gonzalez et al. |
| 8,753,335 B2 | 6/2014 | Moshe et al. |
| 8,771,173 B2 | 7/2014 | Fonger et al. |
| 8,771,260 B2 | 7/2014 | Conlon et al. |
| 8,828,031 B2 | 9/2014 | Fox et al. |
| 8,845,656 B2 | 9/2014 | Skakoon et al. |
| 8,858,590 B2 | 10/2014 | Shelton, IV et al. |
| 8,880,185 B2 | 11/2014 | Hastings et al. |
| 8,882,786 B2 | 11/2014 | Bearinger et al. |
| 8,888,792 B2 | 11/2014 | Harris et al. |
| 8,906,035 B2 | 12/2014 | Zwolinski et al. |
| 8,911,452 B2 | 12/2014 | Skakoon et al. |
| 8,939,897 B2 | 1/2015 | Nobis |
| 8,956,352 B2 * | 2/2015 | Mauch .............. A61B 18/1492 606/27 |
| 8,974,374 B2 | 3/2015 | Schostek et al. |
| 8,986,199 B2 | 3/2015 | Weisenburgh, II et al. |
| 9,005,198 B2 | 4/2015 | Long et al. |
| 9,011,431 B2 | 4/2015 | Long et al. |
| 9,028,483 B2 | 5/2015 | Long et al. |
| 9,036,015 B2 | 5/2015 | Verburgh et al. |
| 9,049,987 B2 | 6/2015 | Conlon et al. |
| 9,078,662 B2 | 7/2015 | Bakos et al. |
| 9,186,203 B2 | 11/2015 | Spivey et al. |
| 9,248,278 B2 | 2/2016 | Crosby et al. |
| 9,271,796 B2 | 3/2016 | Buysse et al. |
| 9,295,485 B2 | 3/2016 | Conlon et al. |
| 9,339,328 B2 | 5/2016 | Ortiz et al. |
| 9,427,255 B2 | 8/2016 | Griffith et al. |
| 9,668,725 B2 | 6/2017 | Beaven |
| 9,788,885 B2 | 10/2017 | Long et al. |
| 9,788,888 B2 | 10/2017 | Bakos et al. |
| 9,861,272 B2 | 1/2018 | Pell et al. |
| 9,883,910 B2 | 2/2018 | Conlon et al. |
| 10,004,558 B2 | 6/2018 | Long et al. |
| 2001/0023333 A1 | 9/2001 | Wise et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Muller et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0082551 A1 | 6/2002 | Yachia et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0018373 A1 | 1/2003 | Eckhardt et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0125770 A1 * | 7/2003 | Fuimaono ............ A61N 1/0563 607/5 |
| 2003/0130564 A1 | 7/2003 | Martone et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |

(56) References Cited

U.S. PATENT DOCUMENTS

| | | |
|---|---|---|
| 2003/0171651 A1 | 9/2003 | Page et al. |
| 2003/0176880 A1 | 9/2003 | Long et al. |
| 2003/0187351 A1 | 10/2003 | Franck et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0138747 A1 | 7/2004 | Kaladelfos |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260315 A1 | 12/2004 | Dell et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0070947 A1 | 3/2005 | Franer et al. |
| 2005/0080413 A1 | 4/2005 | Canady |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216036 A1 | 9/2005 | Nakao |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0240249 A1 | 10/2005 | Tu et al. |
| 2005/0250983 A1 | 11/2005 | Tremaglio et al. |
| 2005/0250987 A1 | 11/2005 | Ewers et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0261711 A1 | 11/2005 | Okada et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |

(56) References Cited

U.S. PATENT DOCUMENTS

| | | |
|---|---|---|
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0241691 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0000550 A1 | 1/2007 | Osinski |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0027469 A1 | 2/2007 | Smith et al. |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0049800 A1 | 3/2007 | Boulais |
| 2007/0049902 A1 | 3/2007 | Griffin et al. |
| 2007/0049968 A1 | 3/2007 | Sibbit et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0078439 A1 | 4/2007 | Grandt et al. |
| 2007/0079924 A1 | 4/2007 | Saadat et al. |
| 2007/0083192 A1 | 4/2007 | Welch |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156116 A1 | 7/2007 | Gonzalez |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173686 A1 | 7/2007 | Lin et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0191904 A1 | 8/2007 | Libbus et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0225554 A1 | 9/2007 | Maseda et al. |
| 2007/0233040 A1 | 10/2007 | Macnamara et al. |
| 2007/0244356 A1 | 10/2007 | Carrillo, Jr. et al. |

(56) References Cited

U.S. PATENT DOCUMENTS

| | | |
|---|---|---|
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0265494 A1 | 11/2007 | Leanna et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0082108 A1 | 4/2008 | Skakoon et al. |
| 2008/0086172 A1 | 4/2008 | Martin et al. |
| 2008/0091068 A1 | 4/2008 | Terliuc |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125765 A1 | 5/2008 | Berenshteyn et al. |
| 2008/0125774 A1 | 5/2008 | Palanker et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147056 A1* | 6/2008 | van der Weide et al. ...... 606/33 |
| 2008/0150754 A1 | 6/2008 | Quendt |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0208280 A1 | 8/2008 | Lindenthaler et al. |
| 2008/0214890 A1 | 9/2008 | Motai et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287801 A1 | 11/2008 | Magnin et al. |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0300571 A1 | 12/2008 | LePivert |
| 2008/0306493 A1 | 12/2008 | Shibata et al. |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0030278 A1 | 1/2009 | Minakuchi |
| 2009/0054728 A1 | 2/2009 | Trusty |
| 2009/0062788 A1 | 3/2009 | Long et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082627 A1 | 3/2009 | Karasawa et al. |
| 2009/0082776 A1 | 3/2009 | Cresina |
| 2009/0082779 A1 | 3/2009 | Nakao |
| 2009/0093690 A1 | 4/2009 | Yoshizawa |
| 2009/0112059 A1 | 4/2009 | Nobis |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0163770 A1 | 6/2009 | Torrie et al. |
| 2009/0177031 A1 | 7/2009 | Surti et al. |
| 2009/0177219 A1 | 7/2009 | Conlon |
| 2009/0182325 A1 | 7/2009 | Werneth et al. |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |
| 2009/0198253 A1 | 8/2009 | Omori |
| 2009/0209990 A1 | 8/2009 | Yates et al. |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227999 A1 | 9/2009 | Willis et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0292167 A1 | 11/2009 | Kimoto |
| 2009/0306470 A1 | 12/2009 | Karasawa et al. |
| 2009/0322864 A1 | 12/2009 | Karasawa et al. |
| 2009/0326332 A1 | 12/2009 | Carter |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049223 A1 | 2/2010 | Granja Filho |
| 2010/0056862 A1 | 3/2010 | Bakos |

(56) References Cited

U.S. PATENT DOCUMENTS

| | | |
|---|---|---|
| 2010/0056864 A1 | 3/2010 | Lee |
| 2010/0076451 A1 | 3/2010 | Zwolinski et al. |
| 2010/0076460 A1 | 3/2010 | Taylor et al. |
| 2010/0081875 A1 | 4/2010 | Fowler et al. |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152725 A1 | 6/2010 | Pearson et al. |
| 2010/0152746 A1 | 6/2010 | Ceniccola et al. |
| 2010/0160906 A1* | 6/2010 | Jarrard .............. A61B 18/1492 606/33 |
| 2010/0191050 A1 | 7/2010 | Zwolinski |
| 2010/0191267 A1 | 7/2010 | Fox |
| 2010/0198149 A1 | 8/2010 | Fox |
| 2010/0198248 A1 | 8/2010 | Vakharia |
| 2010/0198254 A1 | 8/2010 | Schaeffer |
| 2010/0210906 A1 | 8/2010 | Wendlandt |
| 2010/0217367 A1 | 8/2010 | Belson |
| 2010/0249700 A1 | 9/2010 | Spivey |
| 2010/0256628 A1 | 10/2010 | Pearson et al. |
| 2010/0261994 A1 | 10/2010 | Davalos et al. |
| 2010/0268025 A1 | 10/2010 | Belson |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2011/0077476 A1 | 3/2011 | Rofougaran |
| 2011/0087224 A1 | 4/2011 | Cadeddu et al. |
| 2011/0093009 A1 | 4/2011 | Fox |
| 2011/0098694 A1 | 4/2011 | Long |
| 2011/0098704 A1 | 4/2011 | Long et al. |
| 2011/0106221 A1 | 5/2011 | Neal, II et al. |
| 2011/0112434 A1 | 5/2011 | Ghabrial et al. |
| 2011/0112527 A1 | 5/2011 | Hamilton, Jr. et al. |
| 2011/0115891 A1 | 5/2011 | Trusty |
| 2011/0152610 A1 | 6/2011 | Trusty et al. |
| 2011/0152878 A1 | 6/2011 | Trusty et al. |
| 2011/0152888 A1 | 6/2011 | Ho et al. |
| 2011/0152923 A1 | 6/2011 | Fox |
| 2011/0160514 A1 | 6/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0282149 A1 | 11/2011 | Vargas et al. |
| 2011/0284014 A1 | 11/2011 | Cadeddu et al. |
| 2011/0285488 A1 | 11/2011 | Scott et al. |
| 2012/0004502 A1 | 1/2012 | Weitzner et al. |
| 2012/0029335 A1 | 2/2012 | Sudam et al. |
| 2012/0078266 A1 | 3/2012 | Tyson, Jr. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101331 A1 | 4/2012 | Gilad et al. |
| 2012/0101413 A1 | 4/2012 | Beetel et al. |
| 2012/0109122 A1 | 5/2012 | Arena et al. |
| 2012/0116155 A1 | 5/2012 | Trusty |
| 2012/0116266 A1 | 5/2012 | Houser et al. |
| 2012/0149981 A1 | 6/2012 | Khait et al. |
| 2012/0179148 A1 | 7/2012 | Conlon |
| 2012/0191075 A1 | 7/2012 | Trusty |
| 2012/0191076 A1 | 7/2012 | Voegele et al. |
| 2012/0197246 A1* | 8/2012 | Mauch .............. A61B 18/1492 606/33 |
| 2012/0220998 A1 | 8/2012 | Long et al. |
| 2012/0220999 A1 | 8/2012 | Long |
| 2012/0221002 A1 | 8/2012 | Long et al. |
| 2012/0289857 A1 | 11/2012 | Toth et al. |
| 2013/0030430 A1 | 1/2013 | Stewart et al. |
| 2013/0090666 A1 | 4/2013 | Hess et al. |
| 2013/0138091 A1 | 5/2013 | Coe et al. |
| 2013/0158348 A1 | 6/2013 | Nobis et al. |
| 2013/0172672 A1 | 7/2013 | Iddan et al. |
| 2013/0231530 A1 | 9/2013 | Lien et al. |
| 2013/0245356 A1 | 9/2013 | Fernandez et al. |
| 2013/0261389 A1 | 10/2013 | Long |
| 2013/0267834 A1 | 10/2013 | McGee |
| 2013/0331649 A1 | 12/2013 | Khait et al. |
| 2014/0031813 A1 | 1/2014 | Tellio et al. |
| 2014/0039492 A1 | 2/2014 | Long |
| 2014/0052126 A1 | 2/2014 | Long et al. |
| 2014/0052216 A1 | 2/2014 | Long et al. |
| 2014/0121678 A1 | 5/2014 | Trusty et al. |
| 2014/0243597 A1 | 8/2014 | Weisenburgh, II et al. |
| 2014/0343360 A1 | 11/2014 | Shohat et al. |
| 2015/0032132 A1 | 1/2015 | Harris et al. |
| 2015/0100064 A1 | 4/2015 | Skakoon et al. |
| 2015/0230858 A1 | 8/2015 | Long et al. |
| 2016/0074056 A1 | 3/2016 | Conlon |
| 2016/0100879 A1 | 4/2016 | Long |
| 2016/0128759 A1 | 5/2016 | Long et al. |
| 2016/0296280 A1 | 10/2016 | Long |
| 2016/0338731 A1 | 11/2016 | Griffith et al. |
| 2017/0049508 A1 | 2/2017 | Long et al. |
| 2017/0086937 A1 | 3/2017 | Tellio et al. |
| 2017/0119465 A1 | 5/2017 | Long et al. |
| 2018/0042661 A1 | 2/2018 | Long et al. |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0499491 A2 | 8/1992 |
| EP | 0589454 A2 | 3/1994 |
| EP | 0464479 B1 | 3/1995 |
| EP | 0529675 B1 | 2/1996 |
| EP | 0773003 A1 | 5/1997 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A1 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |

(56) References Cited

FOREIGN PATENT DOCUMENTS

| | | |
|---|---|---|
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| EP | 2659847 A1 | 11/2013 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | H06269460 A | 9/1994 |
| JP | 8-29699 A | 2/1996 |
| JP | H 9-75365 A | 3/1997 |
| JP | H 10-24049 A | 1/1998 |
| JP | 3007713 B2 | 2/2000 |
| JP | 2000/107197 A | 4/2000 |
| JP | 2000245683 A | 9/2000 |
| JP | 2001-526072 A | 12/2001 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2005-296063 A | 10/2005 |
| JP | 2006517843 A | 8/2006 |
| JP | 2006297005 A | 11/2006 |
| JP | 2006-343510 A | 12/2006 |
| JP | 2007-20806 A | 2/2007 |
| JP | 2007-125264 A | 5/2007 |
| JP | 2007-516792 A | 6/2007 |
| JP | 2010/503496 A | 2/2010 |
| JP | 2012515018 A | 7/2012 |
| NL | 1021295 C2 | 2/2004 |
| SU | 194230 | 5/1967 |
| SU | 980703 | 12/1982 |
| WO | WO 84/01707 A1 | 5/1984 |
| WO | WO 86/07543 A1 | 12/1986 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 94/22383 | 10/1994 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/22996 | 4/2000 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/035537 A2 | 3/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/135577 A2 | 11/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/034103 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/080062 A2 | 7/2008 |
| WO | WO 2008/101075 A2 | 8/2008 |
| WO | WO 2008/101086 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A2 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO-2009132190 A2 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |
| WO | WO 2012/031204 A2 | 3/2012 |
| WO | WO 2012/071526 A2 | 5/2012 |
| WO | WO-2012068505 A1 | 5/2012 |
| WO | WO 2013/044378 A1 | 4/2013 |

OTHER PUBLICATIONS

Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.

(56) References Cited

OTHER PUBLICATIONS

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure NOTES Surgery With Company's Toolbox," Jun.

(56) References Cited

OTHER PUBLICATIONS 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).

Hakko Retractors, obtained Aug. 25, 2009 (5 pages).

Zadno et al., "Linear Superelasticity in Cold-Worked Ni—Ti," Engineering Aspects of Shape Memory Alloys, pp. 414-419 (1990).

How Stuff Works "How Smart Structures Will Work," http://science.howstuffworks.com/engineering/structural/smart-structure1.htm; accessed online Nov. 1, 2011 (3 pages).

Instant Armor: Science Videos—Science News—ScienCentral; http://www.sciencentral.com/articles/.view.php3?article_id=218392121; accessed online Nov. 1, 2011 (2 pages).

Stanway, Smart Fluids: Current and Future Developments. Material Science and Technology, 20, pp. 931-939, 2004; accessed online Nov. 1, 2011 at http://www.dynamics.group.shef.ac.uk/smart/smart.htm (7 pages).

Jolly et al., Properties and Applications of Commercial Magnetorheological Fluids. SPIE 5th Annual Int. Symposium on Smart Structures and Materials, 1998 (18 pages).

Rutala et al. "Guideline for Disinfection and Sterilization in Healthcare Facilities, 2008" (available at http://www.cdc.gov/hicpac/Disinfection_Sterilization/13_11sterilizingPractices.html).

Bewley et al., "Spinning" in ASM Handbook, vol. 14B, Metalworking: Sheet Forming (2006).

Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.

Davalos, et al., "Tissue Ablation with Irreversible Electroporation," Annals of Biomedical Engineering, 33.2 (2005): 223-231.

International Preliminary Report on Patentability for PCT/US2013/052250, dated Feb. 3, 2015 (10 pages).

Written Opinion for PCT/US2013/052250, dated Oct. 29, 2013 (9 pages).

European Examination Report for 13750419.7, dated Nov. 8, 2016 (7 pages).

Maxim Integrated Application Note 3977: Class D Amplifiers: Fundamentals of Operation and Recent Developments, Jan. 31, 2007.

\* cited by examiner

FLEXIBLE EXPANDABLE ELECTRODE AND METHOD OF INTRALUMINAL DELIVERY OF PULSED POWER

BACKGROUND

Electrical ablation therapy has been used in medicine for the treatment of undesirable tissue, such as, for example, diseased tissue, cancer, malignant and benign tumors, masses, lesions, and other abnormal tissue growths. Apparatuses, systems, and methods for conventional ablation therapies may include electrical ablation therapies, such as, for example, high temperature thermal therapies including, focused ultrasound ablation, radiofrequency (RF) ablation, and interstitial laser coagulation, chemical therapies in which chemical agents are injected into the undesirable tissue to cause ablation, surgical excision, cryotherapy, radiation, photodynamic therapy, Moh's micrographic surgery, topical treatments with 5-fluorouracil, and laser ablation.

Drawbacks of conventional electrical ablation therapies include risk of permanent damage to healthy tissue surrounding undesirable tissue due to exposure to thermal energy and/or lack of controlled energy generated by an electrical ablation device. As such, when undesirable tissue occurs or originates at or near critical structures and surgical resection presents an increased risk of morbidity associated with damage to that critical structure, conventional electrical ablation therapies may be an unsatisfactory alternative. At times, the ability to apply controlled energy to ablate cells within a target zone may be affected by one or more characteristics of the target zone and/or available application positions provided by ablative electrodes. Solutions to address the above issues are often invasive and conflict with optimal surgical outcomes. Accordingly, minimally invasive electrical ablation therapy capable of accurately targeting ablative electrodes to a target site and delivering controlled energy to ablate cells within a target zone while retaining necessary infrastructure of the surrounding tissue is desirable.

SUMMARY

In one general aspect, the various embodiments are directed to an electrical ablation device. One embodiment of the electrical ablation device includes an elongate member having therealong disposed a first electrode extending along an axis. The first electrode has a proximal end configured to couple to an energy source and a surface configured to couple to a tissue treatment region and delivery ablative energy. A first expandable portion extends along the axis and defines a first perimeter of the first electrode and has an associated first diameter with respect to the axis. The first expandable portion includes a first framework comprising at least one first framework member. The first framework is selectively expandable to transition the first expandable portion from a contracted state to an expanded state. The first framework is selectively contractible to transition the first expandable portion from the expanded state to the contracted state. When the first framework is expanded, the first diameter is expanded and the first expandable portion is transitioned from the contracted state to the expanded state. When the first framework is contracted, the first diameter is contracted and the first expandable portion is transitioned from the expanded state to the contracted state.

In another general aspect, a method of treating tissue using the electrical ablation devices described herein includes delivering the first electrode to a tissue treatment region that includes a biological lumen and expanding the first electrode. The first electrode is contacted to a wall of the lumen proximal to tissue to be treated. Tissue is treated by applying one or more sequences of electrical pulse to the first electrode to induce cell death in the tissue by irreversible electroporation.

FIGURES

The various embodiments of electrical ablation devices, systems, and methods thereof described herein may be better understood by considering the following description in conjunction with the accompanying drawings.

Figure 28A:
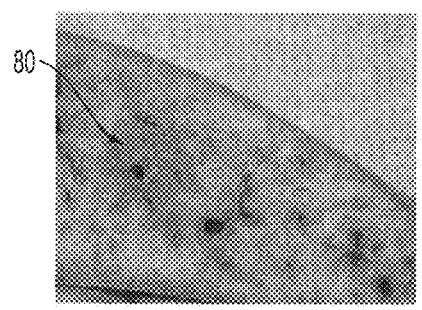
Figure 28B:
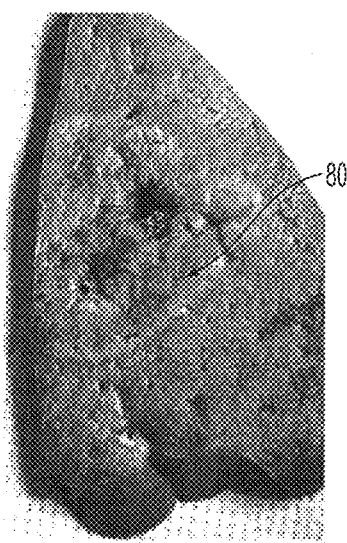

FIGS. 28A-B includes photographs of porcine liver tissues after receiving electrical ablation according to certain embodiments described herein.

Figure 29:
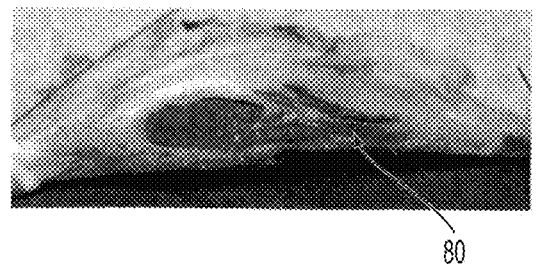

FIG. 29 includes a photograph of porcine heart tissue after receiving electrical ablation according to certain embodiments described herein.

Figure 30:
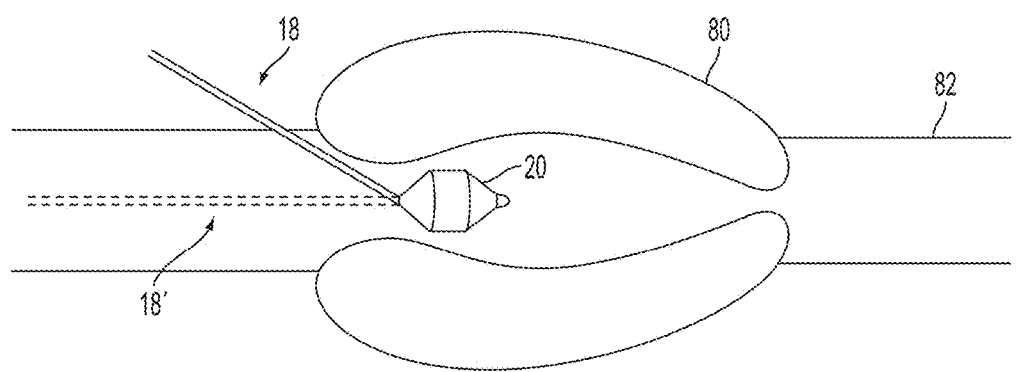

FIG. 30 is a graphical representation of a use of the electrical ablation system according to certain embodiments described herein.

DESCRIPTION

The present disclosure relates generally to the field of electrosurgery. In particular, the present disclosure relates to, although not exclusively, electrosurgical devices. More particularly, the present disclosure relates to, although not exclusively, electrical ablation systems, devices, and methods.

This disclosure describes various elements, features, aspects, and advantages of various embodiments of electrical ablation systems, devices, and methods thereof. It is to be understood that certain descriptions of the various embodiments have been simplified to illustrate only those elements, features and aspects that are relevant to a more clear understanding of the disclosed embodiments, while eliminating, for purposes of brevity or clarity, other elements, features and aspects. Any references to "various embodiments," "certain embodiments," "some embodiments," "one embodiment," or "an embodiment" generally means that a particular element, feature and/or aspect described in the embodiment is included in at least one embodiment. The phrases "in various embodiments," "in certain embodiments," "in some embodiments," "in one embodiment," or "in an embodiment" may not refer to the same embodiment. Furthermore, the phrases "in one such embodiment" or "in certain such embodiments," while generally referring to and elaborating upon a preceding embodiment, is not intended to suggest that the elements, features, and aspects of the embodiment introduced by the phrase are limited to the preceding embodiment; rather, the phrase is provided to assist the reader in understanding the various elements, features, and aspects disclosed herein and it is to be understood that those having ordinary skill in the art will recognize that such elements, features, and aspects presented in the introduced embodiment may be applied in combination with other various combinations and sub-combinations of the elements, features, and aspects presented in the disclosed embodiments. It is to be appreciated that persons having ordinary skill in the art, upon considering the descriptions herein, will recognize that various combinations or sub-combinations of the various embodiments and other elements, features, and aspects may be desirable in particular implementations or applications. However, because such other elements, features, and aspects may be readily ascertained by persons having ordinary skill in the art upon considering the description herein, and are not necessary for a complete understanding of the disclosed embodiments, a description of such elements, features, and aspects may not be provided. As such, it is to be understood that the description set forth herein is merely exemplary and illustrative of the disclosed embodiments and is not intended to limit the scope of the invention as defined solely by the claims.

All numerical quantities stated herein are approximate unless stated otherwise, meaning that the term "about" may be inferred when not expressly stated. The numerical quantities disclosed herein are to be understood as not being strictly limited to the exact numerical values recited. Instead, unless stated otherwise, each numerical value is intended to mean both the recited value and a functionally equivalent range surrounding that value. At the very least, and not as an attempt to limit the application of the doctrine of equivalents to the scope of the claims, each numerical parameter should at least be construed in light of the number of reported significant digits and by applying ordinary rounding techniques. Notwithstanding the approximations of numerical quantities stated herein, the numerical quantities described in specific examples of actual measured values are reported as precisely as possible.

All numerical ranges stated herein include all sub-ranges subsumed therein. For example, a range of "1 to 10" is intended to include all sub-ranges between and including the recited minimum value of 1 and the recited maximum value of 10. Any maximum numerical limitation recited herein is intended to include all lower numerical limitations. Any minimum numerical limitation recited herein is intended to include all higher numerical limitations. Additionally, in some illustrative embodiments, a parameter, measurement, diversion, or range may be given. It is to be understood that any such parameter, measurement, diversion, or range is provided as an illustrative example or instance of an embodiment and is not intended to limit that or other embodiments.

As generally used herein, the terms "proximal" and "distal" generally refer to a clinician manipulating one end of an instrument used to treat a patient. The term "proximal" generally refers to the portion of the instrument closest to the clinician. The term "distal" generally refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

As generally used herein, the term "ablation" generally refers to removal of cells either directly or indirectly by supply of energy within an electric field and may include removal by loss of cell function, cell lysis, necrosis, apoptosis, and/or irreversible electroporation. "Ablation" may similarly refer to creation of a lesion by ablation. Additionally, the terms "undesirable tissue," "target cells," "diseased tissue," "diseased cells," "tumor," "cell mass" and the like are generally used throughout to refer to cells removed or to be removed, in whole or in part, by ablation and are not intended to limit application of the systems, devices, or methods described herein. For example, such terms include ablation of both diseased cells and certain surrounding cells, despite no definite indication that such surrounding cells are diseased. The terms similarly include ablation of cells located around a biological lumen such as a vascular, ductal, or tract area, for example, to create a margin for a surgeon to resect additional cells by ablation or other method.

According to certain embodiments, an ablation system generally comprises first and second electrodes coupled to an energy source operative to generate an electric field between the first and second electrodes when such electrodes are contacted to tissue and energized. An electrical current supplied to the electric field is conducted between the first and second electrode through the tissue. Without wishing to be bound to any particular theory, it is believed the electrical current propagates through conductive tissue at least partially via electron and/or electrolytic carriers. Electrical ablation devices may generally comprise one or more electrodes configured to be positioned at or near undesirable tissue (e.g., target cells, target site, treatment site, diseased tissue, diseased cells, tumor, cell mass) in a tissue treatment region (e.g., a target region). In general, the electrodes may comprise an electrically conductive portion (e.g., medical grade stainless steel, gold plated, etc.) and may be configured to electrically couple to an energy source. Once positioned at or near undesirable tissue, an energizing potential may be applied to the electrodes to create an electric field to which the undesirable tissue is exposed. The energizing potential (and the resulting electric field) may be characterized by various parameters, such as, for example, frequency, amplitude, pulse width (duration of a pulse or pulse length), and/or polarity. Depending on the desired application, for example, the diagnostic or therapeutic treatment to be rendered, a particular electrode may be configured either as an anode or a cathode, or a plurality of electrodes may be configured with at least one electrode configured as an anode and at least one other electrode configured as a cathode. Regardless of the initial polarity configuration, the polarity of the electrodes may be reversed by reversing the polarity of the output of the energy source. In some embodiments, an exogenous electrolyte may be applied to tissue prior to ablation to increase conductivity. In certain embodiments, application of an exogenous electrolyte may increase or decrease an effective area or density of an electric field.

In certain embodiments, a suitable energy source may comprise an electrical waveform generator. The energy source generates an electric field having a suitable characteristic waveform output in terms of frequency, amplitude, pulse width, and polarity. Electrodes may be energized with DC voltages and conduct currents at various frequencies, amplitudes, pulse widths, and polarities. The electrodes may also be energized with time-varying voltages and currents at amplitudes and frequencies suitable for rendering the desired therapy. A suitable energy source may comprise an electrical waveform generator adapted to deliver DC and/or time-varying energizing potentials characterized by frequency, amplitude, pulse width, and/or polarity to the electrodes. The electric current flows between the electrodes and through the tissue proportionally to the potential (e.g., voltage) applied to the electrodes. In various embodiments, supplied electric current is provided by the energy source and comprises a pulse sequence applied to tissue. For example, an energy source may supply various waveforms in one or more pulse sequences tailored to the desired application. Commonly owned U.S. patent application Ser. No. 13/036,908, filed Feb. 28, 2011, titled "ELECTRICAL ABLATION DEVICES AND METHODS," and U.S. patent application Ser. No. 13/352,495, filed Jan. 18, 2012, titled "ELECTRICAL ABLATION DEVICES AND METHODS," disclose many such waveforms, pulse sequences, and methods of application thereof for electrical ablation treatment, the contents of which are herein incorporated by reference.

In one embodiment, the energy source may be configured to produce RF waveforms at predetermined frequencies, amplitudes, pulse widths, and/or polarities suitable for thermal heating and/or electrical ablation of cells in the tissue treatment region. One example of a suitable RF energy source may be a commercially available conventional, bipolar/monopolar electrosurgical RF generator, such as Model Number ICC 350, available from Erbe, GmbH. In one embodiment, the energy source may comprise a microwave energy source configured to produce microwave waveforms at predetermined frequencies, amplitudes, pulse widths, and/or polarities suitable for thermal heating and/or electrical ablation of cells in the tissue treatment region. The microwave power source, such as MicroThermx, available from Boston Scientific Corp., may be coupled to a microwave antenna providing microwave energy in the frequency range from 915 MHz to 2.45 GHz.

In one embodiment, the energy source may be configured to produce destabilizing electrical potentials (e.g., fields) suitable to induce thermal heating and/or irreversible electroporation. The destabilizing electrical potentials may be in the form of bipolar/monopolar monophasic electric pulses suitable for inducing thermal heating and/or irreversible electroporation. A commercially available energy source suitable for generating thermal heating and/or irreversible electroporation electric field pulses in bipolar or monopolar mode is a pulsed DC generator such as Model Number ECM 830, available from BTX Molecular Delivery Systems Boston, Mass. In bipolar mode, the first electrode may be electrically coupled to a first polarity and the second electrode may be electrically coupled to a second (e.g., opposite) polarity of the energy source. Bipolar/monopolar monophasic electric pulses may be generated at a variety of frequencies, amplitudes, pulse widths, and/or polarities. Unlike RF ablation systems, which may require high power and energy levels delivered into the tissue to heat and thermally destroy the tissue, irreversible electroporation may require very little energy applied to the tissue to heat and kill the cells of the undesirable tissue using electric field potentials rather than heat. Accordingly, irreversible electroporation systems may avoid the detrimental thermal effects caused by RF ablation systems.

Various embodiments of the electrical ablation systems, devices, and methods described herein utilize electroporation or electropermeabilization techniques to apply external electric fields (electric potentials) to cell membranes to significantly increase permeability of the plasma membrane of the cell. Irreversible electroporation (IRE) is the process of killing cells by increasing the electrical potential across the cell membrane for a long period of time. IRE provides an effective method for destroying cells while avoiding some of the negative complications of heat-inducing therapies. Namely, IRE kills cells without raising the temperature of the surrounding tissue to a level at which permanent damage may occur to the support structure or regional vasculature. Large destabilizing IRE electric potentials may be in the range of about several hundred to about several thousand volts applied in the tissue to increase the local electric field. The increase in the electric field will increase the membrane potential over a distance of about several millimeters, for example, for a relatively long period of time. The destabilizing electric potential forms pores in the cell membrane when the potential across the cell membrane reaches a critical level causing the cell to die by processes known as apoptosis and/or necrosis.

Application of IRE pulses to cells may be an effective way for ablating large volumes of undesirable tissue with no or minimal detrimental thermal effects to the surrounding healthy tissue. As such, in some embodiments, IRE may be utilized in conjunction with the various electrodes and/or other electrical ablation devices disclosed herein to perform one or more minimally invasive surgical procedures or treatments. Without wishing to be bound to any particular theory, it is believed that IRE destroys cells with no or minimal heat, and thus, may not destroy the cellular support structure or regional vasculature. A destabilizing irreversible electroporation pulse, suitable to cause cell death without inducing a significant amount of thermal damage to the surrounding healthy tissue, may have amplitude in the range of several hundred to several thousand volts and may be generally applied across biological membranes over a distance of several millimeters, for example, for a relatively long duration of 1 μs to 100 ms. Thus, the undesirable tissue may be ablated in-vivo through the delivery of destabilizing electric fields by quickly causing cell necrosis.

In certain embodiments, the energy source may comprise a wireless transmitter to deliver energy to the electrodes using wireless energy transfer techniques via one or more remotely positioned antennas. Those skilled in the art will appreciate that wireless energy transfer or wireless power transmission refers to the process of transmitting electrical energy from an energy source to an electrical load without interconnecting wires. In one embodiment, the energy source may be coupled to first and second electrodes by a wired or a wireless connection. In a wired connection, the energy source may be coupled to the electrodes by way of the electrical conductors. In a wireless connection, the electrical conductors may be replaced with a first antenna coupled the energy source and a second antenna coupled to the electrodes, wherein the second antenna may be remotely located from the first antenna. In one embodiment, the energy source may comprise a wireless transmitter to deliver energy to the electrodes using wireless energy transfer techniques via one or more remotely positioned antennas. As previously discussed, wireless energy transfer or wireless power transmission is the process of transmitting electrical energy from the energy source to an electrical load, e.g., the abnormal cells in the tissue treatment region, without using the interconnecting electrical conductors. An electrical transformer is the simplest example of wireless energy transfer. The primary and secondary circuits of a transformer may not be directly connected and the transfer of energy may take place by electromagnetic coupling through a process known as mutual induction. Power also may be transferred wirelessly using RF energy.

As will be appreciated, the electrical ablation devices, systems, and methods may comprise portions that may be inserted into the tissue treatment region percutaneously (e.g., where access to inner organs or other tissue is done via needle-puncture of the skin). Other portions of the electrical ablation devices may be introduced into the tissue treatment region endoscopically (e.g., laparoscopically and/or thoracoscopically) through trocars or channels of the endoscope, through small incisions, or transcutaneously (e.g., where electric pulses are delivered to the tissue treatment region through the skin).

The systems, devices, and methods for electrical ablation therapy may be adapted for use in minimally invasive surgical procedures to access tissue treatment regions in various anatomic locations, such as, for example, the brain, lungs, breast, liver, gall bladder, pancreas, prostate gland, and various internal body or biological lumen (e.g., a natural body orifice) defined by the esophagus, stomach, intestine, colon, arteries, veins, anus, vagina, cervix, fallopian tubes, and the peritoneal cavity. Minimally invasive electrical ablation devices may be introduced to the tissue treatment region though a small opening formed in the patient's body using a trocar or through a natural body orifice such as the mouth, anus, or vagina using translumenal access techniques known as Natural Orifice Translumenal Endoscopic Surgery (NOTES)™ wherein electrical ablation devices may be initially introduced through a natural body orifice and then advanced to the tissue treatment site by puncturing the walls of internal body lumen. In various embodiments, the electrical ablation system may be adapted to treat undesirable tissue in the brain, lung, breast, liver, gall bladder, pancreas, or prostate gland, using one or more electrodes positioned percutaneously, transcutaneously, translumenally, minimally invasively, and/or through open surgical techniques, or any combination thereof.

In certain embodiments, the systems, devices, and methods may be configured for minimally invasive ablation treatment of cell masses, tumors, growths, or other undesirable tissue. Minimally invasive ablation treatment of undesirable tissue may be characterized by the ability to reduce trauma by accurately targeting undesirable tissue through one or more biological lumens (e.g., a natural body orifice, vascular, duct, or tract area) and applying an electric field to ablate undesirable tissue in a controlled and focused manner while at the same time retaining the cellular infrastructure of the surrounding healthy tissue. According to various embodiments, delivering an electrode to a biological lumen and contacting the lumen wall in a controlled manner provides increased electroablative accuracy which may reduce undesirable lesions, increase probability of desirable circumferential ablation zones, and/or retain necessary infrastructure in surrounding tissue. For example, uniformity and/or density of an electric field over particular regions of the electric field established by various electrodes and/or returns may be more precisely focused or controlled. In certain embodiments, contacting a lumen wall in a controlled manner comprises circumferentially contacting the lumen wall at two or more locations about the circumference of the wall at or near a treatment site, for example, at or along two locations about the circumference of the wall separated by 15°, 30°, 90°, or 180°, for example. Such contact may be continuous, such as contact connecting two points, or discontinuous, such as contact at a first point and at a second point without contact along at least an intervening portion of the lumen wall between the first and second points.

When a tissue treatment region is located at or near a biological lumen, such as a vascular, duct, cavity, orifice, or tract area, for example, minimally invasive electrical ablation devices comprising electrodes may be delivered to the tissue treatment region through an artificial lumen (e.g., channel of endoscope, sheath, sleeve, trocar) and/or through one or more biological lumens, as herein described. In various embodiments, an electrical ablation device (e.g., electrode or an electrode disposed along a probe comprising an elongate member) may be fed through the biological lumen within an endoscope, trocar, sheath, sleeve, or channel, for example. An electrical ablation device may also be configured to be fed through a biological lumen "naked," that is, without assistance from the above instruments. For example, an electrode may be configured to be flexibly fed or directed through one or more biological lumens to the treatment region. In some embodiments, electrodes may be provided along a distal portion of an elongate member comprising a probe. The elongate member may thereby be configured to deliver one or more electrodes to a tissue region. Portions of the elongate member proximal to an electrode may respond to signals from a clinician directing one or more of such positions along a length of the elongate member to move. For example, an elongate member may be responsive to signals to bend at the one or more positions along its length during delivery to a tissue region. Once electrical ablation devices (e.g., electrodes) are delivered or located at or near undesirable tissue in the treatment region, electrodes may be deployed to contact lumen tissue and apply ablative treatment. Such bending, therefore, may assist in navigation and/or placement of the electrical ablation device through or within a biological lumen during delivery, deployment, or during or after ablative treatment.

In particular embodiments, electrodes may be configured to expand circumferentially, for example, when deployed or once located at or near undesirable tissue within a tissue region. Expansion may be the result of deployment, an electrical, mechanical, chemical, or thermal signal actuating an expansion, or, in some instances, a contraction. In some embodiments, electrodes may be configured to expand in at least one dimension. For example, electrodes may be configured to expand in diameter. Electrodes may further be configured to expand in length, such as extending a length of the electrode. In some embodiments, an extension in length may be independent of an expansion in diameter. For example, electrodes may expand in length without expanding in diameter or may expand in diameter without expanding in length. In other embodiments, however, an expansion in diameter or length may be concomitant with an increase or decrease in diameter or length. In certain embodiments, electrodes may be configured to expand only in diameter or length. In various embodiments, electrodes expandable in one or more dimensions may be similarly configured to contract in one or more dimensions. Such electrodes may be said to be transitionable between an expanded state and a contracted state. In some embodiments, transitions between one or more expanded states and one or more contracted states may be in response to a signal provided by a clinician. Thus, in some embodiments, a clinician may selectively transition an electrode to a desired expanded and/or contracted state to beneficially fit an electrode to a desired application, such as a procedure and/or biological structure. In certain instances, selecting an expanded state may provide increase contact about a circumference of a lumen thereby creating a more precisely defined electric field and increasing controllability of electric field potentials, for example. In various embodiments, an electrode may comprise an antenna, such as a microwave antenna, wherein undesirable tissue positioned adjacent to or near the antenna may be more fully exposed to ablative energy when the electrode is in an expanded state compared to a contracted state. For example, a diameter, length, and/or surface area of an electrode comprising antenna may be increased in the expanded state such undesirable tissue is fully exposed to ablative energy.

Figure 1:
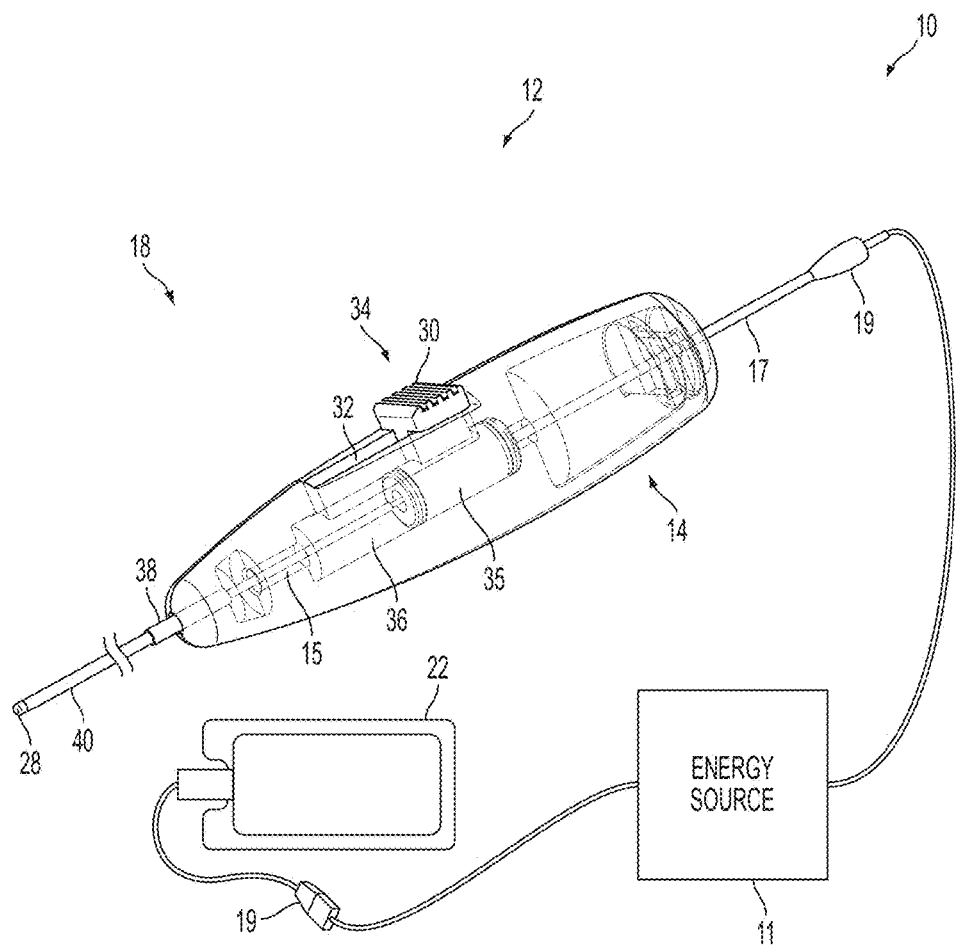
FIG. 1 illustrates an electrical ablation system according to certain embodiments described herein.

An electrical ablation system 10 incorporating an electrical ablation device 12 according to one embodiment is illustrated in FIG. 1 and includes an elongate member 18 having therealong disposed a connector 19 configured to couple to an energy source 11, a handle 14, a first electrode 21 (not shown), and a distal tip 28. The handle 14 is configured to provide a clinician a point of manipulation to, for example, manipulate and/or maneuver the elongate member 18. The elongate member 18 includes a conductive structure comprising a lead wire 17 through which energy may be transmitted between the connector 19 and the first electrode 21. It is to be appreciated, however, that in some embodiments the elongate member 18 or electrode 21 may be wirelessly coupled to the energy source 11 or may be coupled to the energy source 11 by various methods known in the art. The handle 14 includes a sheath 40 extending from a distal end thereof through a protective sleeve 38. In the embodiment illustrated, the handle 14 and sheath 40 define a channel 15 through which the conductive structure extends. The sleeve 38 may comprise an insulative material, such as heat shrink, for example, and may be fixed to the handle 14. As illustrated, the sheath 40 comprises a flexible insulator such as a nonconductive material by which electric current may be insulated. As is to be appreciated, respective lengths of the elongate member 18 and/or the sheath 40 will most generally depend on the desired application; thus, the lengths illustrated herein are not intended to be drawn to scale.

Figure 2:
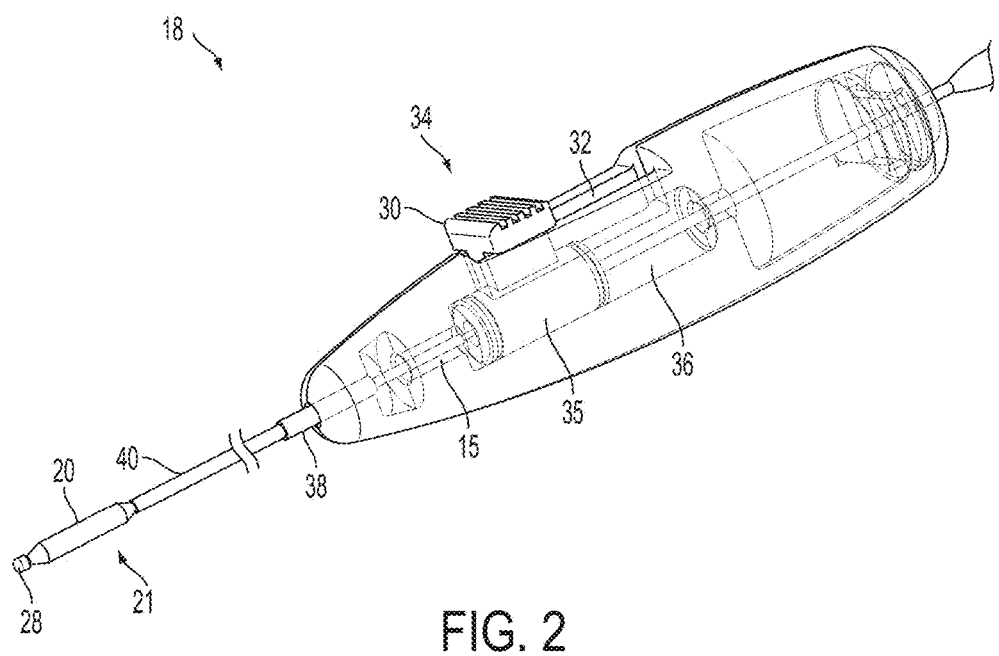
FIG. 2 illustrates an embodiment of the handle and elongate member illustrated in FIG. 1 with the expandable portion of the electrode deployed and in an expanded state according to certain embodiments described herein.

In FIG. 1, the first electrode 21 (not shown) is in a withdrawn or non-deployed position and is received within the sheath 40. In various embodiments, the distal portion of the elongate member 18, including the sheath 40, may be configured as a delivery platform from which the first electrode 21 may be manipulatively delivered to a treatment region and subsequently deployed to a treatment site. Accordingly, the handle 14 may include an actuator configured to deploy the first electrode (not shown). In the illustrated embodiment, the handle 14 includes and actuator comprising a slide member 30 configured to be slidable through an aperture 32 and is coupled to a slide assembly 34 comprising a piston 35, which is translatable through a cylinder 36 defined within the handle 14. The slide assembly 34 is operatively coupled to the elongate member 18 such that movement of the slide member 30 retracts or advances the distal portion of the elongate member 18 relative to the distal end of the handle 14. In this embodiment, the sheath 40 is fixed relative to the distal end of the handle 14. However, in certain embodiments, the sheath 40 may be movable relative to the distal end of the handle 14 using an actuator, such the slide member 30, for example. The distal portion of the elongate member 18 may be deliverable to a tissue treatment region by, for example, physically advancing the elongate member 18, such as feeding the elongate member 18 into a patient within the sheath 40, artificial lumen, natural orifice, or biological lumen. In some embodiments, one of which is illustrated in FIG. 2, the elongate member 18 may be advanced to deploy and expose the first electrode 21 beyond the distal end of the handle 12, sheath 40, endoscope (not shown), or other delivery device (e.g., a channel). In certain embodiments, the elongate member 18 may also be retracted relative to the distal end of the handle 14, sheath 40, endoscope (not shown), or other delivery device. As shown in FIGS. 1 and 2, a clinician may reposition the slide member 30 to selectively extend and retract the elongate member 18 relative to the distal end of the sheath 40. For example, distally positioning the slide member 30 extends the elongate member 18 relative to the distal end of the sheath, exposing the first 21 electrode, and subsequently repositioning the slide member 30 proximally retracts the elongate member 18 relative to the distal end of the sheath, receiving the first electrode 21 within the sheath 40.

The electrical ablation system 10 illustrated in FIG. 1 further comprises a second electrode 22 coupled to the energy source 11. In this particular embodiment, the second electrode 22 comprises a return pad. In various embodiments, the second electrode 22 may be a return pad, needle, clamp, second elongate member, or second electrode disposed along the distal portion of the elongate member 18. Notably, those having ordinary skill in the art will appreciate that the optimal type of second electrode 22 will generally be dependent upon the desired application of the system 10.

In some embodiments, electrodes 21, 22 may deliver electric field pulses to the undesirable tissue. Such electric field pulses may be characterized by various parameters, such as, for example, pulse shape, amplitude, frequency, pulse width, polarity, total number of pulses and duration. In various embodiments, the electric field pulses may be sufficient to induce thermal heating in the undesirable tissue without inducing irreversible electroporation in the undesirable tissue. In certain embodiments, the electric field pulses may be sufficient to induce irreversible electroporation in the undesirable tissue. The effects induced may depend on a variety of conditions, such as, for example, tissue type, cell size, and electrical field pulse parameters. For example, the transmembrane potential of a specific tissue type may primarily depend on the amplitude of the electric field and pulse width.

In one embodiment, the input to the energy source 11 may be connected to a commercial power supply by way of a plug (not shown). The output of the energy source 11 is coupled to electrodes 21, 22, which may be energized using an activation switch (not shown) on the handle 14, or an activation switch mounted on a foot activated pedal (not shown). The energy source 11 may be configured to generate electric pulses at a predetermined frequency, amplitude, pulse width, and/or polarity that are suitable to induce thermal heating in the undesirable tissue in the treatment region or induce irreversible electroporation to ablate substantial volumes of undesirable tissue in the treatment region. The polarity of the DC pulses may be reversed or inverted from positive-to-negative or negative-to-positive a predetermined number of times to induce irreversible electroporation to ablate substantial volumes of undesirable tissue in the treatment region.

In some embodiments, one or more series of electric pulses may be applied to induce IRE. In one embodiment, a timing circuit may be coupled to the output of the energy source 11 to generate electric pulses. The timing circuit may comprise one or more suitable switching elements to produce the electric pulses. For example, the energy source 11 may produce a series of m electric pulses (where m is any positive integer) of sufficient amplitude and duration less than the necrotic threshold to induce thermal heating in the undesirable tissue when the m electric pulses are applied and a series of n electric pulses (where n is any positive integer) of sufficient amplitude and duration to induce irreversible electroporation suitable for tissue ablation when the n electric pulses are applied. In various embodiments, the electric pulses may have a fixed or variable pulse width, amplitude, and/or frequency.

The electrical ablation device 12 may be operated either in bipolar mode, e.g., the electrodes are relatively close to one another, or monopolar mode, e.g., the electrodes are far apart and one electrode typically has a much larger surface area. For example, the electrodes 21, 22 may be employed in a bipolar electrical ablation system in which the first electrode 21 has a positive polarity relative to the other electrode 22. In monopolar mode, a grounding pad, as illustrated in FIG. 1, for example, may be substituted for one of the electrodes 21, 22. In some embodiments, the second electrode 22 comprises one of an electrode disposed along the elongate member 18, an electrode disposed along a second elongate member, a needle electrode, or a clamp. In some embodiments, the electrodes 21, 22 may be employed in a biphasic electrical ablation system in which the polarity of each electrode 21, 22 alternates. In biphasic mode, the first electrode 21 may be electrically connected to a first polarity and the second electrode 22 may be electrically connected to the opposite polarity. In monopolar mode, the first electrode 21 may be coupled to a prescribed voltage and the second electrode 22 may be set to ground. The energy source 11 may be configured to operate in either a biphasic or monophasic mode with the electrical ablation system 10. In bipolar mode, the first electrode 21 may be electrically connected to a prescribed voltage of one polarity and the second electrode 22 may be electrically connected to a prescribed voltage of the opposite polarity. When more than two electrodes are used, the polarity of the electrodes may be alternated so that any two adjacent electrodes may have either the same or opposite polarities.

Returning to FIG. 2, the first electrode 21 includes an expandable portion 20 expandable in at least one dimension. In particular, the expandable portion 20 illustrated in FIG. 2 includes an expanded diameter compared to the diameter of the expandable portion 20 when received within the sheath 40. When received within the sheath 40, the sheath 40 defines a channel having a diameter greater than that of the received expandable portion 20. However, when deployed from the sheath 40 and expanded, as illustrated in FIG. 2, the expandable portion 20 is expanded such that the diameter of the expandable portion 20 is greater than that of the channel defined within the sheath 40. Thus, when received, the expandable portion 20 is in a contracted state and when deployed and/or expanded the expandable portion 20 is in an expanded state.

In various embodiments, the elongate member 18 may be flexible along all or a portion of its length. Such flexible portions may be bendable, deformable, or elastic, for example. Flexible portions may also be conditionally flexible or conditionally rigid, for example. In some embodiments, the elongate member 18 comprises flexible portions which may be mechanically bendable such that portions of the elongate member 18 are pivotable in response to a signal or otherwise manipulatable. In some embodiments, the elongate member 18 may be proximally and/or distally advanced relative to the handle 14. A distal advance of the elongate member 18 relative to the distal end of the handle 14, for instance, may coincide with a distal advance of the elongate member 18 relative to the proximal end of the handle 14. In certain embodiments, when advancing the elongate member 18 increases a length of the elongate member 18, distal to the distal end of the handle 14, the increase in length coincides with a decrease in length of the elongate member 18 proximal to the proximal end of the handle 14. In various embodiments, a proximal advance of the elongate member 18 relative to the distal end of the handle 14 coincides with a proximal advance of the elongate member 18 relative to the proximal end of the handle 14. In certain embodiments, when advancing the elongate member 18 decreases a length of the elongate member 18 distal to the distal end of the handle 14, the decrease in length coincides with an increase in length of the elongate member 18 proximal to the proximal end of the handle 14. While the elongate member 18 illustrated in FIG. 1 is depicted as having a general cylindrical shape, it is to be appreciated that the elongate member 18 may have any suitable shape or cross-section. For example, cross-sections of the elongate member 18 or portions thereof may be generally defined by circular, triangular, rectangular, pentagonal, hexagonal, or any of the suitable bounded shape, be it a regular geometric shape or irregular, for example.

In some embodiments, one or more portions of the elongate member 18 may be coiled, nested, or otherwise contained within the handle 14 or a distal portion of the elongate member 18. In some such embodiments, a distal advance of the elongate member 18 relative to the distal end of the handle 14 does not coincide with a distal advance of the elongate member 18 relative to the proximal end of the handle 14. In one such embodiment, a proximal advance of the elongate member 18 relative to the distal end of the handle 14 does not coincide with a proximal advance of the elongate member 18 relative to the proximal end of the handle 14. In certain embodiments, when advancing the elongate member 18 increases a length of the elongate member 18 distal to the distal end of the handle 14, the length of the elongate member 18 proximal to the proximal end of the handle 14 remains the same. In one such embodiment, when advancing the elongate member 18 decreases a length of the elongate member 18 distal to the distal end of the handle 14, the length of the elongate member 18 proximal to the proximal end of the handle 14 remains the same.

In certain embodiments, the electrical ablation system 10 comprises a relatively flexible elongate member 18 and may be introduced, directed, and delivered to a tissue treatment region within the sheath 40. The sheath 40 may be a hollow bore, such as a tube, for example. In some embodiments, the sheath 40 is semi-rigid and may be used to accurately deliver the first electrode 21 to a tissue treatment region. The elongate member 18 may be translatable through the hollow bore to alternately withdraw and deploy one or more electrode(s) 21, 22 or a portions thereof. In some embodiments, the elongate member 18 comprises an extendable portion, such as an extendable length. The length may be extendable by, for example, distally extending the elongate member 18 such that the elongate member 18 distally elongates relative to the distal end of the handle 14, thus advancing or deploying the first electrode 21 or a portion thereof. Similarly, an actuator, such as slide assembly 34, may be provided to extend the elongate member 18. For example, the elongate member 18 may advance or deploy the first electrode 21 or a portion thereof by distally feeding an additional length of the elongate member 18. It is to be appreciated that extension of the elongate member 18 is not limited to feeding additional elongate member 18 distally from the handle 14. In some embodiments, a portion of the elongate member 18 may extend by moving a first portion of the elongate member 18 relative to a second portion of the elongate member 18. The first and second portions of the elongate member 18 may flank both sides of a nested portion such that a relative movement between the first and second portions of the elongate member 18 may thereby result from a telescopic extension or retraction of a length of the elongate member 18, increasing or decreasing the overall length of the elongate member 18. The first and second portions of the elongate member 18 may also flank both sides of a folded portion of the elongate member 18 such that a relative movement between the first and second portions of the elongate member 18 may thereby result from a folding or unfolding of the folded portion resulting in an accordion-like extension or retraction of a length of the elongate member 18. Relative movement between first and second portions may be accomplished by any known mechanism, such as pulleys, reciprocating extension members, slide mounts, gears, and/or tracks, for example. In some embodiments, the elongate member 18 may advance or deploy the first electrode 21 by progressive release of a bias within the elongate member 18. In the embodiment illustrated in FIG. 1, an actuator is configured to deploy the first electrode 21 from the distal end of the sheath 40. However, in other embodiments, a sheath 40 may not be provided and the clinician may deploy the first electrode 21 by advancing the first electrode 21 from the distal end of an endoscope, trocar, or other artificial lumen configured to receive the elongate member 18 and deliver the first electrode 21 to the target region. In these and other embodiments, the sheath 40 or artificial lumen may be configured to deploy or withdraw the first electrode 21 or portion thereof by advancing or retracting to expose or receive the first electrode 21 or portion thereof.

Figure 3:
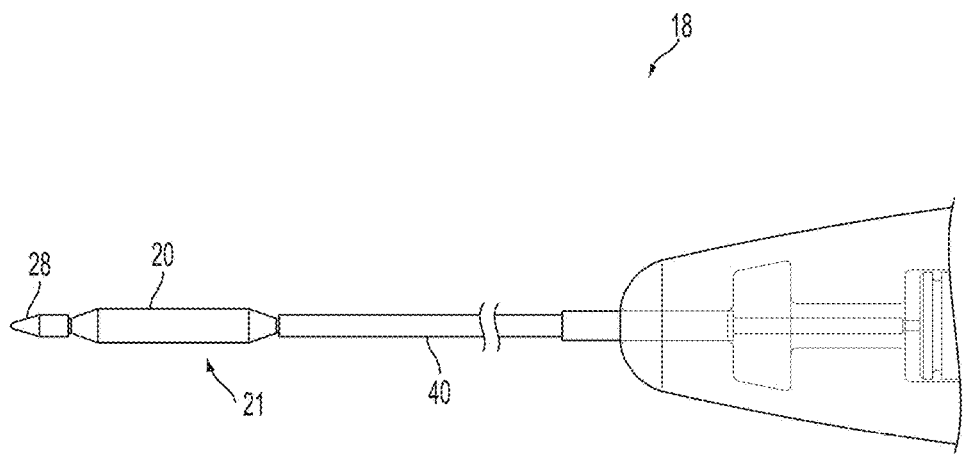
FIG. 3 illustrates an electrode disposed along a distal portion of an elongate member wherein the expandable portion is deployed and in an expanded state according to certain embodiments described herein.

As previously described, the elongated member 18 may comprise a distally located tip 28. In certain embodiments, the tip 28 may include an insulator configured to resist conduction of electric current. It is to be appreciated that tips 28 of various dimensions may be provided to suit particular applications. For example, in some embodiments, the length of the tip 28 may be longer than the first electrode 21 while in other embodiments the length of the tip 28 may be shorter than the first electrode 21. Tips 28 of various lengths may beneficially increase stability of the first electrode 21 during ablation or assist delivery of the first electrode 21 by, for example, increasing steerability of the elongate member 18. In various embodiments, a diameter of the tip 28 may be greater than or less than a diameter of the first electrode 21 in a contracted state. In some such embodiments, the tip 28 may comprise multiple diameters. Tips 28 comprising multiple diameters may be configured to assist in delivery, placement, and/or positioning of the first electrode 21. For example, contours provided about the multiple diameters of the tip 28 may be designed to anchor or fitably position the first electrode 21 at or near a treatment site. Such contours may also include one or more surface features configured to grippably engage tissue at or near a treatment site. In various embodiments, the tip 28 comprises a distal end configured to assist in delivery, placement and/or positioning of the first electrode 21. For example, a distal end of the tip 28 may comprise a dull or blunt end, as illustrated in FIG. 1, for example. In some embodiments, the distal end of the tip 28 comprises a comparatively sharp point configured to direct the elongate member 18 along surfaces and within channels. FIG. 3 illustrates an embodiment comprising such a tip 28. In particular, FIG. 3 illustrates a first electrode 21 disposed along a distal portion of the elongate member 18. The distal end of the elongate member 18 comprises a tip 28. The tip 28 is tapered to a comparatively sharp point. It is to be appreciated the degree of taper may be more or less than depicted in FIG. 1 or 3, depending on the desired application. In some embodiments, the tip 28 may be a sharp point configured to pierce tissue and/or anchor the first electrode 21. The tip 28 may also comprise a thin catheter configured to drain fluid, for example. As will be explained in more detail below, in certain embodiments, the tip 28 may perform any number of functions such as sensory functions (e.g., optics, temperature, location, etc.) and/or electrolyte delivery. It is to be appreciated that in some embodiments an electrode 21 may comprise the tip 28 and be configured to deliver or receive electric current. For example, in some embodiments, the tip 28 may be a needle electrode.

In various embodiments, the slide assembly 34 is operatively coupled to the sheath 40 such that movement of the slide member 30 in a first direction advances the sheath 40 relative to the distal end of the handle 14 and movement of the slide member 30 in a second direction retracts the sheath relative to the distal end of the handle 14. In some embodiments, the sheath may be retractable relative to the distal end of the handle 14 to expose or deliver the first electrode 21 to a deployed position at or near a treatment site. In some embodiments, the sheath 40 may be advanceable relative to the distal end of the handle 14 to envelope or withdraw the first electrode 21 to a withdrawn position. It will be appreciated that the elongate member 18 may be advanceable by arrangements other than the slide member 30, such as a lever, trigger, actuator, or button, for example, and advancement or retraction may be effectuated manually, electrically, and/or mechanically, for example. In one embodiment, the elongate member 18 may be advanced or retracted by increasing or decreasing a length of the elongate member 18. For example, one or more electrodes 21 or other portions of the elongate member 18 may comprise an adjustable length comprised of an elastic or otherwise extendable or compressible material such that an adjustment of the length effectuates an advancement or retraction of the elongate member 18. In some embodiments, a distal advancement of the elongate member 18 deploys the first electrode 21 to target tissue and a proximal retraction of the elongate member 18 withdraws the first electrode 21 from target tissue. In some embodiments, one or more actuators may be configured to deploy the first electrode 21 to a treatment region, to withdraw the first electrode 21 from a treatment region, to extend or flex the first electrode 21, and/or to transition the expandable portion 20 between contracted and expanded states. In some embodiments, multiple transitions may be actuated by the same or different actuators. For example, an actuation signal to transition between a contracted state and an expanded state may be coupled with an actuation signal to withdraw or deploy the first electrode 21.

Figure 4:
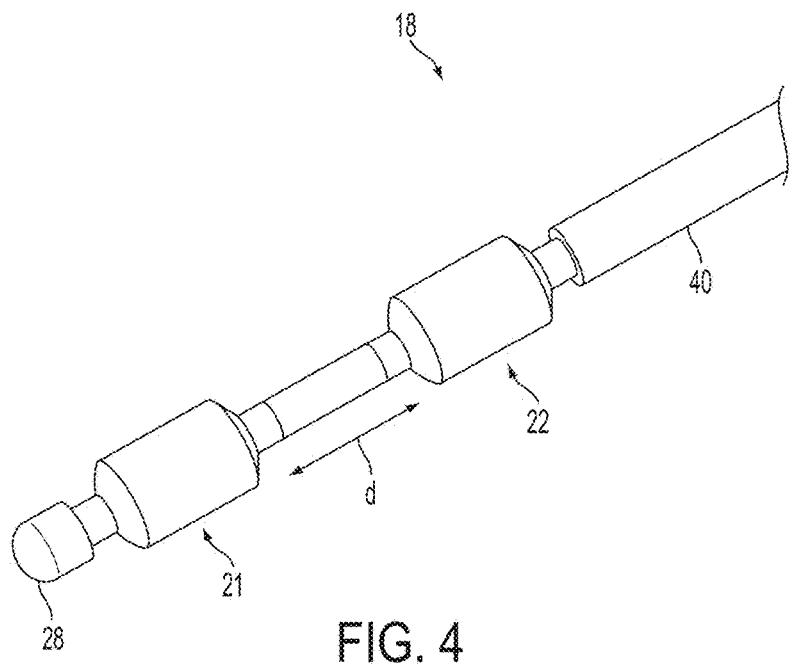
FIG. 4 illustrates two electrodes disposed along a distal portion of an elongate member wherein the respective expandable portions are deployed and in expanded states according to certain embodiments described herein.

In various embodiments, first and second electrodes 21, 22 may be disposed along the distal portion of the elongate member 18 and may be employed to more precisely define a treatment area to, for example, ablate undesirable tissue while reducing muscle contractions in adjoining tissues. FIG. 4 illustrates an embodiment of the electrical ablation device 12 and system 10 depicted in FIG. 1 comprising a first electrode 21 and a second electrode 22 disposed along the distal portion of the elongate member 18. The first electrode 21 may be configured as the positive electrode and the second electrode 22 may be configured as the negative electrode. The first electrode 21 may be electrically coupled to the conductive structure, which may be coupled to the positive terminal of the energy source 11. The second electrode 22 may be electrically coupled to a conductive structure, such as an electrically conductive lead or wire, which may be coupled to the negative terminal of the energy source 11. The conductive structures may be electrically insulated from each other and surrounding structures, except for the electrical connections to the respective electrodes 21, 22. The first and second electrodes 21, 22 may be deployed using actuation methods similar to those described with respect to the first electrode 21. For example, the first electrode 21 may be withdrawn or advanced by repositioning of slide member (not shown) or other actuator. The second electrode 22 may similarly be withdrawn or advanced by repositioning of the same or different slide member or other actuator. In some embodiments, advancing the first electrode 21 or second electrode 22 deploys respective electrodes 21, 22 from the distal end of the sheath 40. One or both electrodes 21, 22 may be coupled to the slide member, or additional slide members may be provided to advance and/or withdraw the electrodes 21, 22 and/or to deploy the electrodes 21, 22. Additionally, it is to be appreciated that, in certain embodiments, first and second electrodes 21, 22 may be selectively deployable. Thus, a clinician may optionally use the first electrode 21 or the second electrode 22 by selectively deploying only the first electrode 21 or only the second electrode 22. In this way, the clinician may independently locate additional electrodes before or after applying power to the first electrode 21 and/or second electrode 22, thus, providing flexibility to create a variety of electric fields during a single insertion of the electrical ablation device 12. It is to be appreciated that, in some embodiments, the identities of the first electrode 21, second electrode 22, or additional electrodes may be selectively changed or switched. For example, in one embodiment, the functionality of the first electrode 21 may be disabled and the identity of the second electrode 22 switched to the previous identity of the first electrode 21.

In some embodiments, where the elongate member comprises multiple electrodes, the distance "d" between electrodes may be adjustable. Referring again to FIG. 4, the illustrated embodiment includes an adjustable distance between the first electrode 21 and second the electrode 22. Such an adjustable distance may be adjustable between 2 mm and 25 mm, for example, and may be used to flexibly confine a treatment zone. A clinician may accordingly adjust the distance "d" between electrodes 21, 22 prior to use by, for example, inserting one or more extenders or inserts between electrodes 21, 22. Multiple extenders or inserts of suitable lengths may be provided to allow a clinician to customize the distance between electrodes 21, 22 and tailor the length to a desired use. In some embodiments, the distance between to electrodes 21, 22 may be adjusted by advancing or rotating the first electrode 21 relative to the second electrode 22 by actuation of one or more slides or actuators located on the handle 14. For example, electrodes 21, 22 may be threadably or slidably disposed along the elongate member about threads or along another track. In various embodiments, the intervening length of elongate member between electrodes 21, 22 may expand thereby increasing the distance.

Figure 5:
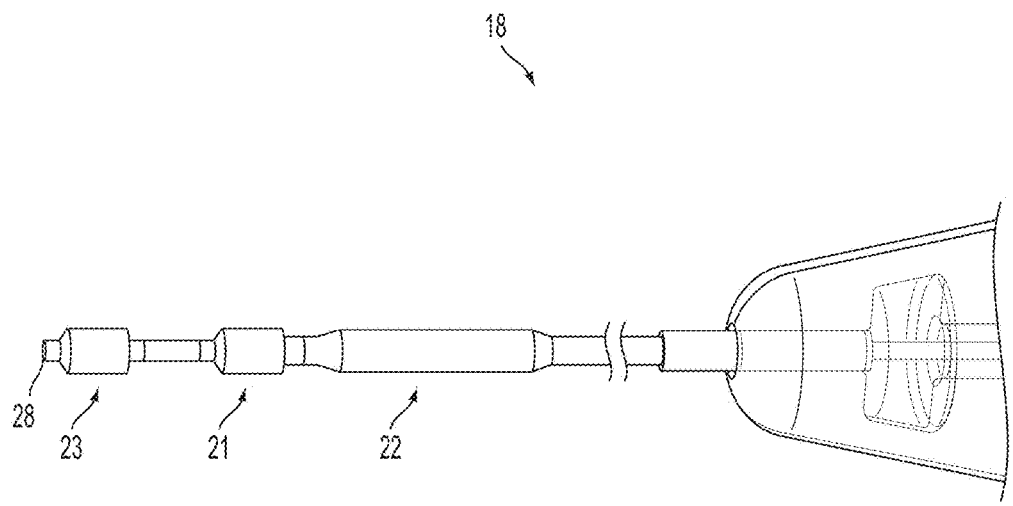
FIG. 5 illustrates three electrodes disposed along a distal portion of an elongate member wherein respective expandable portions are deployed and in expanded states according to certain embodiments described herein.

FIG. 5 illustrates an additional embodiment of the electrical ablation device 12 and system depicted in FIG. 1 comprising a first electrode 21 and a second electrode 22 disposed along the distal portion of the elongate member 18. The electrodes 21, 22 are illustrated in various levels of expanded states. For example, both the first electrode 21 and second electrode 22 are expanded about the axis. The second electrode 22, however, is also extended along the axis and comprises a length greater than the first electrode 21. In some embodiments, asymmetrical electrodes may be provided such that when the electrodes 21, 22 expand, the electrodes 21, 22 comprise divergent dimensions. In other embodiments, however, symmetrical electrodes (e.g., electrodes comprising the same or substantially similar dimensions) may be provided. Divergent dimensions may include, for example, different diameters and/or lengths, as illustrated in FIG. 5. Selection of optimal divergent dimensions with respect to two or more electrodes 21, 22 will, in general, be dictated by the desired application. Notably, and as will be explained in more detail below, first 21 and second electrodes 22 may diverge in one or more dimensions as the result of selective expansion, as a by-product of a method of expansion, or due to construction. For example, the length of the first electrode 21 in the contracted state may or may not be the same length of the second electrode 22 in the contracted state, however, the length of the two electrodes 21, 22 may nonetheless be the same length in respective expanded states. The embodiment illustrated in FIG. 5 further comprises a third electrode 23 disposed along the distal portion of the elongate member 18. The third electrode 23, is distal to the first electrode 21 and, in some embodiments, may be attachable to the first electrode 21 at a connection at or near the distal tip 28 of the elongate member 18 or first electrode 21. In some embodiments, the third electrode 23 is configured as a return or comprises a polarity different from that of the first 21 and/or second electrode 22. In other embodiments, however, the third electrode 23 is configured to extend the electrical identity of the first 21 or second electrode 22.

According to the various embodiments of electrical ablation systems, devices, and methods disclosed herein, electrodes 21 may comprise flexible and/or expandable portions. In some instances, such flexible and/or expandable portions may include a framework comprising one or more framework members providing, which may provide structure to the flexible and/or expandable portions. In various embodiments, a framework defines a selectively expandable perimeter and/or diameter of the expandable portion and may include one or more energy delivery surfaces configured to contact tissue and deliver ablative energy. Herein, the generalized shape and periphery surfaces of expandable and/or flexible portions may be generally referred to as a basket. It is to be appreciated that the electrodes in FIGS. 2-5 and 7 include one or more generalized depictions of baskets and, thus, are not intended to limit the disclosure with respect to appearance or construction of frameworks. Notably, as will become apparent below, flexible and/or expandable portions may comprise baskets comprising various framework constructions having various perimeters and cross-sections including helical, circular, triangular, rectangular, pentagonal, hexagonal, or any other suitable shape, be it a regular geometric shape or irregular, for example. Furthermore, while, in some embodiments, a framework may comprise, for example, a conductive sleeve having an energy delivery surface configured to apply ablative energy that may or may not be dressed about internally arranged framework members, baskets in various other embodiments need not comprise a continuous surface. For example, in certain embodiments, a basket comprises a discontinuous surface defined by a framework of two or more framework members which include tissue contract regions having energy delivery surfaces configured to contact tissue and deliver ablative energy. It is also to be appreciated that while embodiments of electrodes 21 and portions thereof may be referred to as expandable or flexible, the two are not mutually exclusive. Indeed, in certain embodiments, an electrode 21 comprises a flexible portion and an expandable portion wherein at least a portion of the expandable portion comprises at least a portion of the flexible portion. That is, at least a portion of the expandable portion and the flexible portion of the electrode 21 overlap. In some embodiments, however, the expandable portion and the flexible portion may not overlap or may only overlap when the electrode 21 is in the contracted state or the expanded state.

Framework members may be configured to flex or bend in one or more directions and may comprise flexible materials exhibiting elastic and/or reflexive properties. For example, framework members may comprise materials such as plastics, polymers, alloys, metallics, or other elastics including superelastics. Framework members may similarly comprise rigid or conditionally rigid materials configures to flex or bend about a joint or socket, for example. In some embodiments, a clinician may decrease trauma associated with directing electrodes through tortuous biological lumens by utilizing a flexible electrode 21. Flexible electrodes 21 may beneficially reach undesirable tissues in target regions that may otherwise be considered inoperable. In various embodiments, flexible electrodes 21 may also increase the contact area between tissue contact regions of the flexible electrodes 21 and undesirable tissue. As those having skill in the art will recognize, flexible electrodes 21 may be especially helpful by providing greater control over an application when, for example, undesirable tissue is partially obstructing a biological lumen.

Figure 6:
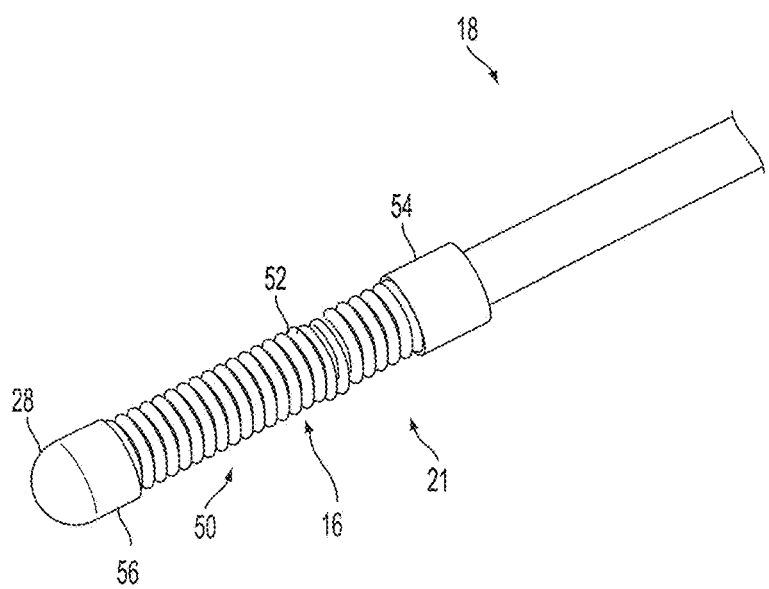
FIG. 6 illustrates a flexible portion of an electrode disposed along a distal portion of an elongate member according to certain embodiments described herein.

FIG. 6 illustrates a flexible portion 16 according to certain embodiments. The flexible portion 16 is disposed along a distal portion of the elongate member 18 and includes a cylindrical framework 50 comprising a coiled framework member 52 (e.g., a spring). The framework 50 extends along a longitudinal axis defined by the flexible portion 16. The framework further comprises a proximal coupler 54 and a distal coupler 56. The proximal coupler 54 and distal coupler 56 are configured to couple the framework member 52 to the elongate member 23 and tip 28. In the embodiment illustrated, the tip 28 provides a blunt and rounded terminus and the flexible portion 16 is flexibly configured for insertion into a biological lumen such that it may flex or bend, for example, in response to curvatures of the lumen. The electrode 21 may also beneficially bend or flex during delivery to a tissue treatment region either through an artificial delivery channel such as an endoscope, trocar, or lumen, for example, or naked (i.e., exposed or not within an artificial delivery channel). In this way, the flexible portion 16 may be flexibly delivered to a target region in a minimally invasive manner.

In various embodiments, electrodes 21 may be expandable in any physical dimension, such as, for example, width or height. In some embodiments, for instance, an expansion of an electrode 21 may be described as an increase in a diameter of the electrode 21. As generally used herein, the term "diameter" generally means a straight line distance between two points located along a perimeter of an expandable portion 20 such that the straight line passes through the axis of the expandable portion 20. The perimeter of an expandable portion 20 may comprise a periphery or external surface of the expandable portion 20. For example, in some embodiments, the framework 50 defines a perimeter of the expandable portion 20 and a diameter may be the distance between two tissue contact regions on opposing sides of the framework. It is to be appreciated that diameter is not limited to a specific geometric shape or cross-section and includes helical, circular, triangular, rectangular, pentagonal, hexagonal, or any other suitable shape, be it a regular geometric shape or irregular, for example.

In addition to expandability and/or flexibility, an electrode 21 may also be extendable. That is, a length of the electrode 21 may be extendable by extending a movable portion of the electrode 21 relative to a fixed portion of the electrode 21. For example, in one embodiment of the flexible electrode 21 illustrated in FIG. 6, a clinician may extend the flexible electrode 21 by actuating a relative movement between the proximal coupler 54 and the distal coupler 56 such that the length of the flexible portion 16 increases. Such an extension may or may not reduce flexibility of the flexible portion 16. As those having skill in the art may recognize, in various embodiments of the electrodes disclosed herein, an extendable length may be utilized by a clinician increase an application area to beneficially reduce trauma that may otherwise result from multiple ablative treatments.

In various embodiments, an electrical ablation device 12 comprises one or more expandable electrodes 21. Expandable electrodes 21, such as those illustrated in FIGS. 2, 3, and 4, for example, may comprise a framework 50 comprising one or more framework members 52. It is to be appreciated that framework members 52 may have an associated first form and an associated second form. In some embodiments, the first form comprises a memory form and the second form comprises a retained form. The retained form may comprise an arrangement or orientation of framework members 52 in an other than memory form. For example, in the retained form, framework members 52 may be deformed, retarded, or otherwise strained as a result of manipulation by, for example, a retaining structure. Manipulation may include stress such as torque, compressive, and/or tension on one or more framework members 52 such that the expandable portion 20 comprises an increased or decreased diameter. In some embodiments, manipulation may result in plastic deformation. In certain embodiments, framework members 52 in the retained form may be transitioned to the memory form by release or removal of a retaining structure retaining the framework members 52 in the retained form. In certain embodiments, framework members 52 in the retained form may also be returned to the memory form by manipulation including application of torque, compression, and/or tension stress on one or more framework members 52 such that the expandable portion 20 and/or framework 50 comprises an increased or decreased diameter.

The degree to which a dimension of an expandable portion 20 may expand may be many multiples of the original value of the dimension. For example, a dimension of an expandable portion 20 in a first state may have a value of 1 and the dimension of the expandable portion 20 in a second state may have a value of 2, 3, 10, 20 or greater, such as 40. In certain embodiments, the degree of expansion is limited only by the length of the expandable portion 20 in the first state. In some embodiments, a variable expansion feature is provided. A variable expansion feature may enable the clinician to adjust the degree to which an electrode 21 expands. For example, a clinician may adjust the degree of expansion to a predetermined diameter before or during a procedure. A variable expansion feature may also be configured to adapt to a procedure or provide feedback to the clinician such that the degree of expansion may be adjusted. For example, the magnitude of an expansion force may be finite and/or nominal after a particular degree of expansion has taken place such that degree of expansion may be limited when external resistance to expansion is at or near a predetermined threshold, for example, when a wall or structure is obstructing a full expansion. Such a variable expansion feature may be further adjustable to tailor to specific applications. For example, an electrode 21 comprising a conductive balloon may be inserted into a lumen and inflated by controllable pressure to substantially conform to the shape of the lumen. Such a complementary shape may increase circumferential contact about the lumen without exerting an invasive force on tissue. Similarly, in various embodiments, framework members 52 retain at least partial flexibility when the expandable portion 20 is in the expanded state. For example, framework members 52 may be flexible inward toward the axis and/or outward of the axis. The elongate member 18 and/or expandable portion 20 may similarly be flexible away from the axis at various angles and directions. In some embodiments, an adaptable feature includes an electrode 21 wherein the length of the expandable portion 20 may be adjustable. For example, in some embodiments, an expandable portion 20 may be withdrawn or received within the sheath 40 such that only the portion of the expandable portion 20 that remains deployed is expanded when the expandable portion 20 is selectively transitioned to the expanded state.

Figure 7:
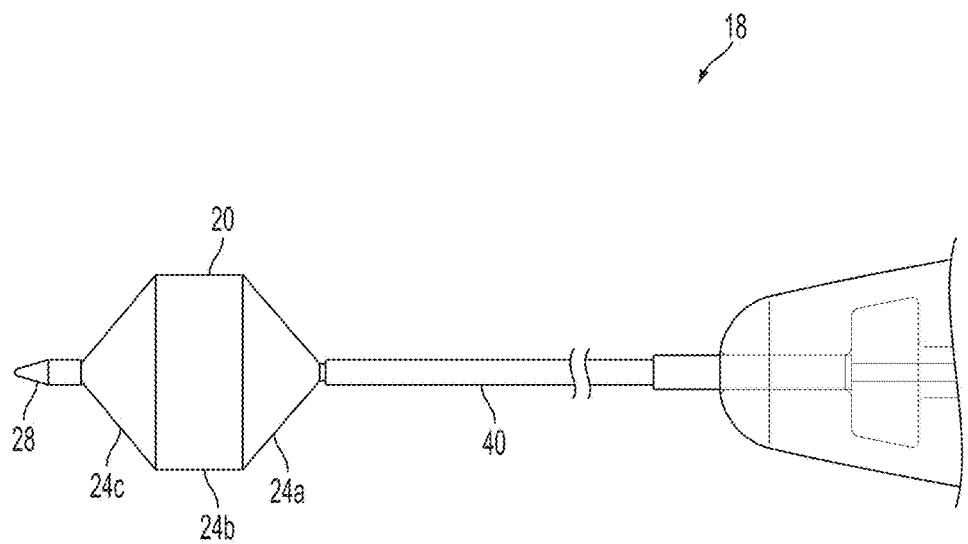
FIG. 7 illustrates a deployed expandable portion of an electrode in an expanded state according to certain embodiments described herein.

FIG. 7 illustrates an embodiment of an expandable portion 20 disposed along an elongate member 18 according to various embodiments. The expandable portion 20 is shown deployed from a sheath 40 and is in an expanded state. A framework 50 defines a general perimeter (e.g., a basket) about an axis of the expandable portion 20 and includes a first tapered length 24a diverging about 50° from the axis, a second length 24b extending substantially parallel to the axis, and a third tapered length 24c converging about 50 degrees toward the axis. In various embodiments, the basket may be representative of a metallic balloon, metallic covering, or an embodiment similar to FIG. 9, 13, or 24, for example, wherein the degree of expansion is a function of the first and/or third tapered lengths and the degree to which the tapered lengths diverge relative to the axis. The elongate member 18 further comprises a distal tip 28 providing a terminus tapered to a sharp point. In the contracted state (not shown) the diameter of the expandable portion 20 is reduced by a factor of at least 8 such that the expandable portion 20 may be received within a channel defined within the sheath 40. When deployed from the distal end of the sheath 40, the expandable portion 20 may be expanded by any disclosed method. As can be seen, the degree of expansion may be a function of the first and/or third tapered lengths 24a,c and the degree to which the tapered lengths 24a,c respectively diverge or converge relative to the axis. For example, increasing or decreasing the degree of divergence or convergence of the first and/or third tapered lengths 24a,c respectively increases or decreases the degree of expansion while also respectively decreasing or increasing the length of the expandable portion 20. Additionally, increasing or decreasing the lengths of the first and/or third tapered lengths 24a,c respectively increases or decreases the degree of expansion. In embodiments where the first and/or third tapered lengths 24a,c may be extendable, for example, the length of the expandable portion 20 may not increase or decrease during a transition between the expanded state and the contracted state. However, in embodiments, wherein the first and/or third tapered lengths 24a,c do not extend, an expansion may decrease the length of the expandable portion 20.

According to various embodiments, electrodes 21 or expandable portions 20 thereof may be selectively transitioned between a contracted state and one or more expanded states. FIGS. 8-25 illustrate various non-limiting embodiments of expandable portions 20 of electrodes 21 comprising frameworks 50 and framework members 52 as well as various non-limiting embodiments of methods of expanding and/or contracting expandable portions 20. Before addressing these embodiments, however, a number of beneficial aspects of these and other embodiments will be introduced to assist those having skill in the art in their understanding of the various embodiments.

In some embodiments, transitioning an expandable portion 20 from a contracted state to an expanded state may be driven by an expansion force. Expansion forces may be applied to one or more framework members 52 to effectuate an expansion. Expansion forces may comprise any known force, such as torque, compression, or tension, for example. In one embodiment, for instance, changes in internal pressure drive transitions using an injectable, such as a solid, liquid, or gas, injected into or released from a cavity defined within a framework 50. Increase in interior pressure may expand the framework 50 to an equilibrium pressure in one or more regions of the framework 50 or may drive further expansion by increasing tension about the cavity of the framework 50. Similarly, contraction forces may be applied to one or more framework members 52 to drive a contraction, such as a contraction between an expanded state and a less expanded state. Contraction forces may comprise any known force, such as torque, compression, and tension, for example, to decrease a dimension. For example, in one embodiment, changes in internal pressure drive transitions using an injectable, such as a solid, liquid, or gas, injected into or released from a cavity defined within a framework 50. Decrease in interior pressure, such as a release of an injectable, may contract the framework 50 to an equilibrium pressure in one or more regions of the framework 50 by relieving tension about the cavity or may drive further contraction by releasing additional injectable, thereby allowing external pressure to compress the framework 50 and occupy the cavity.

In various embodiments, electrical ablation devices 12 may employ compression, tension, and/or rotation to transition electrodes 21 or expandable portions 20 between contracted and expanded states. In some embodiments, compression of framework members 52 may decrease a length of the expandable portion 20 while, at the same time, increase a diameter of the expandable portion 20. For example, compressed framework members 52 may strain, bow, or bend outward of the axis to relieve compressive stress. Compression may also drive a repositioning of framework members 52 within the framework 50 to effectuate a transition that increases a diameter of an expandable portion 20 without decreasing a length of the expandable portion 20. For example, one or more framework members 52 or portions thereof may be urged outward of the axis or along the elongate member 18 resulting in repositioning of those or other framework members 52 and an increase in a dimension of the expandable portion 20. In some embodiments, tension of framework members 52 may increase a length of the expandable portion 20 while, at the same time, decreasing a diameter of the expandable portion 20. For example, otherwise bowed or outward extending framework members 52 may be tensioned to strain, stretch, or straighten inward toward the axis as to relieve tension stress. Tension may also drive repositioning of framework members 52 within the framework 50 to effectuate a transition that increases a diameter of the expandable portion 20 without decreasing a length of the expandable portion 20. For example, one or more framework members 52 or portions thereof may be pulled inward toward the axis or along the elongate member 18 resulting in repositioning of those or other framework members 52 and a decrease in a dimension of the expandable portion 20. In some embodiments, a rotation of a first coupler configured to couple manipulations effectuating relative movements between framework members 52 or portions thereof relative to a second coupler may increases or decreases a distance between framework members 52 or portions thereof. For example, a decrease in the distance may compress one or more intervening portions or other framework members 52 while an increase in the distance may tension one or more intervening portions or framework members 52.

In various embodiments, framework members 52 comprise memory materials. Memory materials may include reflexive and/or elastic materials configured to return to a memory orientation or arrangement following removal of a deformative stress. For example, in some embodiments, framework members 52 are configured to be deformed by a deformative stress above or below an elastic limit and return to a memory form upon removal of the deformative stress and/or subsequent manipulation, such as a change in temperature. In certain embodiments, memory materials include shape memory materials having one-way and/or two-way memory effect. Memory materials may also include materials that may be deformable and reformable by manipulation. For example, a first counter rotation between two portions of a coil may partially unwind the coil while a second counter rotation, opposite of the first, may rewind the coil. Materials having such properties are known in the art and include polymers such as memory foams, plastics, elastomers, and rubbers as well as metallics and alloys. It is to be appreciated that such materials include superelastics and shape memory materials, such as alloys (e.g., NiTi), ceramics, and polymers including gels, foams, and solids. Notably, when framework members 52 comprise memory materials that are poor conductors, conductive materials may be used to establish an electrical path for ablative energy to be transmitted and delivered to tissues. For example, conductive coatings, wires, sleeves, and/or tissue contact regions may be used to transmit and deliver energy to tissue. In some embodiments, elastic limits of framework members 52 may be increased due to arrangement and/or orientation of framework members 52. For example, framework members 52 may comprise configurations of coils or braids comprising increased elastic limits due to, for example, distributed strains.

In various embodiments, framework members 52 a memory form that may be manipulated or otherwise deformed or retained by a retaining force and upon removal of the retaining force, the material at least partially returns to the memory form. Framework members 52 having a memory form may be arranged within the expandable portion 20 in any suitable manner such that the framework members 52 will return to the memory form following removal of a retaining force or upon manipulation. For example, a framework 50 comprising a conductive coating and including framework members 52 comprising a foam polymer may be configured to expand in at least one dimension upon removal of a retaining force and contract in the at least one dimension upon application of the retaining force. In certain embodiments, the retaining force is provided by a channel (e.g., an artificial channel defined within an endoscope, trocar, or sheath) in which the expandable portion 20 is received. Other retaining structures may also be used to apply a retaining force. For example, hooks, latches, constrictable loops, or other retaining mechanisms may be employed in certain embodiments to retain framework members 52 and/or prevent framework members 52 from transitioning to one or more memory forms.

Framework members 52 may individually or collectively have one or more memory forms and/or retained forms. For example, framework members 52 may deform in response to a retaining force and return to a memory form when the retaining force is removed. Alternately, framework members 52 may comprise a first memory form and a second memory form wherein when one or more framework members 52 are in the first memory form the expandable portion 20 is in an expanded state and wherein when one or more of the framework members 52 are in the second memory form, the expandable portion 20 is in a contracted state. In certain embodiments, the memory form may correspond to the expanded state and thus comprises an increased diameter compared to the retained form or may correspond to the contacted state and thus comprises a decreased diameter compared to the retained form. Of course, in some embodiments, a retaining force may be combined with and or coupled to a second, third, or plurality of additionally forces to effectuate an active transition between contracted and expanded states.

Framework members 52 may be configured to deform or strain to reduce a diameter of the expandable portion 20 when framework members 52 are compressed toward the axis or are otherwise retained. In this way, an electrode 21 may be directed to a tissue treatment region within an artificial channel in a contracted state and be expandable upon deployment at or near the tissue treatment site and/or in response to removal of the retaining force. In one embodiment, a first framework member 52 comprising a bias, such as a spring, foam, or other memory material, is biased outward of the axis, such as radially. When the expandable portion 20 is pushed, pulled, or rotated within a channel having a diameter less than a diameter of the expandable portion 20 in the expanded state, the channel compresses the first framework member 52 toward the axis, retaining it in a retained form. However, when the expandable portion 20 is pushed, pulled, or rotated from the channel, the first framework member 52 is no longer retained by the channel and, therefore, transitions to the memory form upon deployment and extends outward of the axis. In a further embodiment, a second framework member 52 extends proximally toward the channel when the expandable portion 20 is deployed and in the expanded state. The second framework member 52 comprises a proximal lip and a distal compression surface coupled to the outward extending portion of the first framework member 52. When the expandable portion 20 is received within the channel, the proximal lip is progressively drawn into the channel, leveraging the distal compression surface toward the axis, compressing the first framework member 52, and decreasing a diameter of the expandable portion 20.

Figure 8:
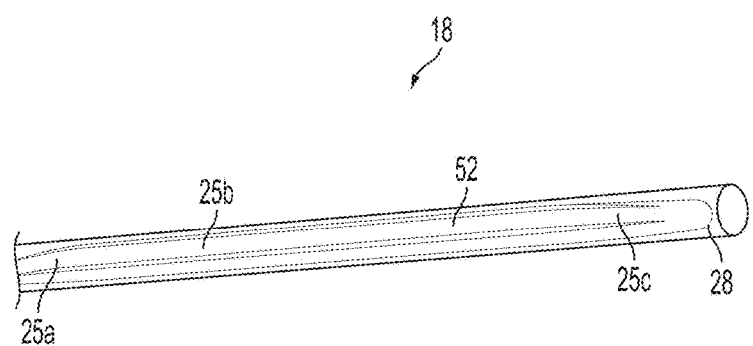
FIG. 8 illustrates a cutaway view of an expandable portion received within a channel defined within a sheath wherein the expandable portion is in a contracted state according to certain embodiments described herein.
Figure 9:
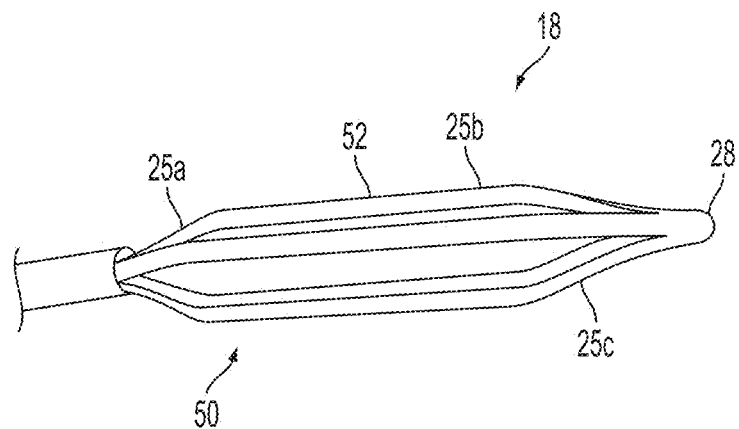
FIG. 9 illustrates the expandable portion illustrated in FIG. 8 deployed from the distal end of the sheath and in an expanded state according to certain embodiments described herein.

FIG. 8 illustrates an expandable portion 20 disposed along a distal portion of an elongate member 18. The expandable portion 20 is in the contracted state and is within an artificial channel defined within a sheath 40. The channel has a diameter less than a diameter of the expandable portion 20 in the expanded state and retains the framework members 52 in a retained form. The sheath 40 is operatively connected to a handle 14 (not shown). The handle includes an actuator (not shown), which may be similar to the slide member 30 illustrated in FIG. 1, configured to deploy and withdraw the expandable portion 20 from the distal end of the sheath 40. In some embodiments, the expandable portion 20 may be deployed by advancing the expandable portion 20 distally of the sheath 40. Accordingly, advancing the expandable portion 20 may comprise proximally withdrawing the sheath 40 or distally advancing the expandable portion 20 relative to the handle 14. When the expandable portion 20 is received within the sheath 40, a retaining force is applied to the expandable portion 20 by the channel, thus, restraining the expandable portion 20 in the contracted state. However, as illustrated in FIG. 9, when the expandable portion 20 is deployed from the sheath 40, the framework members 52 are no longer retained by the channel and, therefore, transition to a memory form. In this embodiment, the memory form corresponds to the expanded state of the expandable portion 20.

Still referring to FIG. 9, the expandable portion may be transitioned to the contracted state by withdrawing the expandable portion 20 within the channel. When the expandable portion 20 in received within the channel, the channel applies a retaining force to the framework members 52, thereby retaining the framework members 52 in the retained form. An active force such as a compression, tension, and/or torque may be employed to withdraw and/or deploy the expandable portion 20. For example, the expandable portion 20 may be pushed, pulled, or rotated from or into the channel. Pushing, pulling, or rotating the expandable portion 20 may further be combined with compression applied by the channel to force framework members 52 to deform toward the axis and transition the expandable portion 20 to the contracted state, as illustrated in FIG. 8. In some embodiments, transitioning the expandable portion 20 to a contracted state comprises applying tension to one or more framework members 52. Tension may also be combined with rotation, for example. In some embodiments, a proximal tension may force framework members 52 to deform toward the axis and may be combined with a distal compression of framework members 52.

The expandable portion 20 in the expandable state illustrated in FIG. 9 includes framework members 52 including a linear portion 25b flanked by a distal tapered portion 25c and a proximal tapered portion 25a. In the memory form, the proximal tapered portion 25a diverges away from the axis at a first angle, and the distal tapered portion 25c converges toward the axis at a second angle. As can be seen, the degree of expansion is a function of the lengths and degree of divergence and convergence of the tapered portions 25a,c. For example, increasing the length of the tapered portions 25a,c increases the diameter of the expandable portion 20. Additionally, the degree of expansion increases as the degree of divergence and convergence approaches 90°. In some embodiments, such an expansion in diameter is also accompanied by a reduction in length of the expandable portion 20. While FIGS. 8 & 9 illustrate a framework 50 comprising four framework members 52 in a basket arrangement, frameworks 50 may include any number of framework members 52. For example, in some embodiments, a framework 50 comprises two framework members 52 extending along the axis. According to the desired application, the diverging and converging tapered lengths and angles they define may be increased to increase the degree of expansion or decreased to decrease the degree of expansion. In certain embodiments, a plurality of 5, 10, 20, or more framework members 52 may extend along the axis and be expandable to a predetermined diameter. In certain embodiments, framework members 52 may be formed from a sheet or tube of framework material. For example, a framework 50 comprising a sheet or tube may be cut or etched, for example with a laser, such that one or more framework members 52 or portions thereof may be extendable away from the axis when the expandable portion 20 is in the expanded state. In certain embodiments, a framework 50 comprises an alloy tube body comprising one or more longitudinal framework members 52 laser etched along the body, and when the expandable portion 20 is in the expanded state, the one or more framework members 52 extend outward of the axis.

The framework members 52 illustrated in FIGS. 8 and 9, may comprise a memory material, such as superelastics. Memory materials comprising superelastics, such as shape memory materials, may be configured to expand or contract to a memory form upon release of a retaining force or upon manipulation. Framework members 52 incorporating superelastics may therefore comprise an associated memory form and an associated retained form. The retained form may correspond to a martensitic conformation while the memory form may correspond to an austenitic conformation. For example, at austenitic temperatures, framework members 52 may be retained by a retaining structure, e.g., compressed within the channel, in a martensitic conformation and return to an austenitic conformation comprising an increased diameter when no longer retained by a retaining structure, e.g., when deployed from the distal end of the sheath 40. Similarly, at martensitic temperatures, framework members 52 may be plastically deformed to a reduced diameter in a martensitic conformation and then returned to an expanded diameter in an austenitic confirmation upon increase to the austenitic transition temperature. Similarly, framework members 52 may be received within the channel of the sheath 40 in an austenitic confirmation and then deployed from the distal end of the sheath in the austenitic confirmation. Once deployed, a retaining force comprising a relative decrease in the distance between framework members 52 or portions thereof or an internal extension extending framework members 52 or portions thereof outward of the axis may compress or tense framework members 52 into a martensitic confirmation comprising an increased diameter. Upon removal of the retaining force at austenitic temperatures, framework members 52 return to an austenitic conformation comprising a reduced diameter. Upon removal of the retaining force at martensitic temperatures, framework members 52 may return to reduced diameter by application of a deformative stress or an increase to austenitic temperatures. In some embodiments, framework members 52 have two-way memory. For example, framework members 52 may comprise at least two memory forms and be transitional between the at least two memory forms in response to manipulation. For instance, in some embodiments, framework members 52 comprise a low temperature memory form and a high temperature memory form. The framework members 52 may thereby be transitioned between the two memory forms via manipulation comprising a change in temperature above and below associated transition temperatures. Of course, as those having ordinary skill in the art may deduce from this disclosure, countless variations of one-way and two-way shape memory may be employed to achieve desired transitions of expandable portions 20 herein described and, therefore, further description of all the possible variations is unnecessarily.

In some embodiments, framework members 52 are arranged as a regular or an irregular grouping of looped coils, braids, or folds occupying a portion of the expandable portion. In various embodiments, framework members 52 may comprise a material, orientation, and/or arrangement imparting the framework members 52 with a memory form when loads are within an associated elastic limit. For example, a framework member 52 may comprise a spring (e.g., a bow, compression, torsion, or tension spring) having an associated memory form and associated elastic limit. The spring may increase or decrease in a dimension in response to an application or removal of a load. When springs are coils or helixes wound about the axis, framework members 52 may be at least partially unwound when the expandable portion 20 is in the contracted state and framework members 52 may be rewound when the expandable portion 20 is in the expanded state. Framework members 52 comprising coils or helixes may also comprise a changed diameter upon application or removal of a load when, for example, a load longitudinally strains a spring. In this way, a clinician may, for example, increase a diameter of a framework member 52 by compressing a compression spring or releasing tension applied to a tension spring. Similarly, a clinician may, for example, decrease a diameter of a framework member 52 by releasing a compressive load applied to a compression spring or apply a tension to a tension spring. Thus, framework members 52 may undergo deformative strains, such as linear or torsion, in a retained form and transition to a memory form upon removal or reversal of a load or force.

Figure 10:
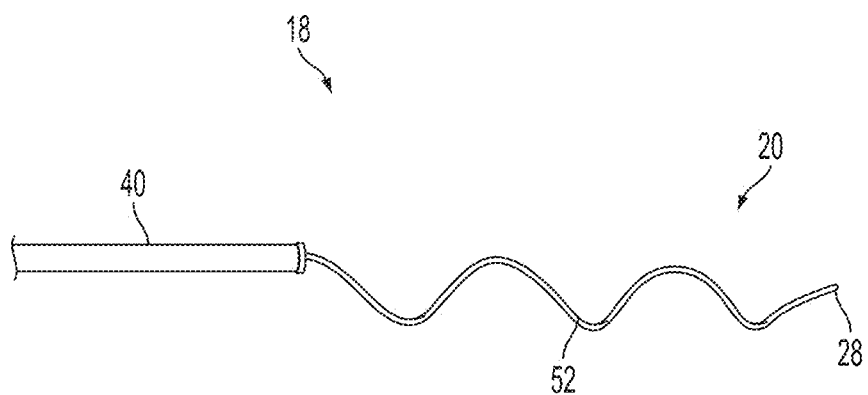
FIG. 10 illustrates a deployed expandable portion in an expanded state according to certain embodiments described herein.

FIG. 10 illustrates an expandable portion 20 disposed along a distal portion of an elongate member 18 comprising a tip 28. The expandable portion 20 is illustrated deployed from a sheath 40 and in an expanded state. A coiled framework member 52 comprising a spring is looped about the axis and is depicted in a memory form comprising an increased diameter. It will be appreciated that the diameter of the expandable portion 20 in FIG. 10 may be configured to increase as a function of the pitch between coils. For example, as pitch decreases and the length of the spring approaches its solid height, the diameter of the spring increases. The expandable portion 20 in FIG. 10 may be transitioned to a contracted state by withdrawing the framework member 52 within a channel defined within the sheath 40 (or a separate channel) comprising a diameter less than the diameter of the expandable portion 20 in the expanded state. For example, when a proximal tension force is applied to the expandable portion 20, the expandable portion 20 is received within the channel forcing the framework member 52 to longitudinally extend, thus, reducing the diameter of the spring and transitioning the framework member 52 into a retained form. While the framework member 52 is retained within the channel, the length of the expandable portion 20 is increased and the diameter of the expandable portion 20 is decreased. When desired, a clinician may subsequently transition the expandable portion 20 from the contracted state to the expanded state (as illustrated in FIG. 9) by deploying the expandable portion 20 from the distal end of the sheath 40. Deploying the expandable portion 20 releases the retaining force and allows the framework member 52 to transition from the retained form to the memory form. In some embodiments, channels may also be fitted with spaced grooves, threads, or tracts, for example, configured to precisely deploy a length of spring or number of coils from the channel.

Figure 11:
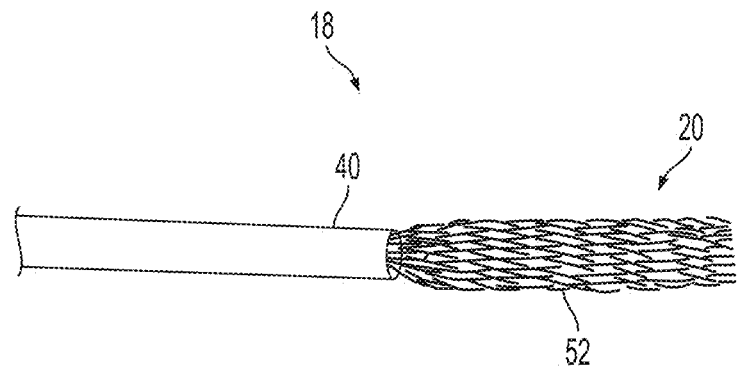
FIG. 11 illustrates a deployed expandable portion transitioning from a contracted state to an expanded state according to certain embodiments described herein.

In various embodiments, framework members 52 may be braided to form one or more baskets along a length of the expandable portion 20. In one embodiment, framework members 52 are braided into a general cylindrical or tube-like arrangement as illustrated in FIG. 11. The expandable portion 20 is shown in the process of deploying from a distal end of a sheath 40 concomitant with a transition between a contracted state and an expanded state. The framework members 52 comprise a conductive braid having an associated retained form and memory form. The framework members 52 are configured to expand to the memory form upon removal of a retaining force, thereby transitioning the expandable portion 20 from the contracted state to the expanded state. For example, when the expandable portion 20 is in the expanded state, it may be proximally withdrawn and received within a channel comprising a lesser diameter and transitioned to the contracted state. Tension stress is applied to the braid when the expandable portion 20 is proximally withdrawn into the lesser diameter of the channel, urging the braid to increase in length while decreasing in diameter. Thereafter, the reduced diameter of the channel maintains compression on the braid and retains the tension stress within the braid. In the contracted state, the expandable portion 20 is deliverable to a tissue treatment region within the channel. Once delivered to the tissue treatment region, the expandable portion 20 may be deployed from the distal end of the sheath 40, thereby decompressing the braid and relieving the tension stress. Consequently, the braid decreases in length and expands about its diameter when the braid is transitioned from the retained form to the memory form. Thus, removal of the retaining force relieves the tension stress within the braid resulting in a reduction in the length of the braid and an increase in a diameter of the braid. As such, the expandable portion 20 may transition from the contracted state to the expanded state upon removal of the retaining force.

In additional embodiments, framework members 52 may be arranged in one or more concentric coils (e.g., loops or wrappings) of framework members 52 arranged about the axis. An outer band of the coil may thereby be rotatable relative to an inner band of the coil such that the expandable portion 20 may be transited between contracted and expanded states by relative rotations between the bands. Such framework members 52 may further comprises an associated memory form and an associated retained form such that a relative rotation between bands comprises a retain force and transitions the expandable portion 20 from the expanded state to the contracted state and a release of the retaining force transitions the expandable portion 20 from the contracted state to the expanded state. In other embodiments, however, a relative rotation between bands may transition the expandable portion 20 from the contracted state to the expanded state and a release of a retaining force may transition the expandable portion 20 from the expanded state to the contracted state. It is to be appreciated that multiple coils comprising multiple bands rotatable relative to one another such that various diameters along the length of the expandable portion 20 may be used to adjustable diameters of the expandable portion 20 to meet various applications.

In various embodiments, electrical ablation devices 12 comprise movable portions. Movable portions may comprise framework couplers and/or movable elements including rings, blocks, or collars disposed about or along the elongate member 18. Movable portions may be slidable along a tract, rotatable about threads, or movable along a distance of the elongate member 18, for example. Elongate members 18 and/or expandable portions 20 may further comprise an adjustable distance such that a movable portion does not physically transition along an elongate member 18 but rather moves as a result of a decrease or increase in the relative distance between the movable portion and another movable portion or position along the elongate member 18 or with respect to the axis. For example, an elongate member 18 may comprise an adjustable distance wherein an adjustment in the distance results in a first movable portion moving relative to a second movable portion. In certain embodiments, the distance between movable portions may be adjusted by extending or retracting a folded or nested portion of the adjustable distance, for example. Extending or retracting may be accomplished by, for example, relative rotations, release of a bias, and/or application of counter or relative forces between two portions. In one embodiment, an electric ablation device 12 comprises a movable portion such as a block, ring, coupler, or other element comprising an abutment surface. The element may be configured to be movable along an elongate member 18 and abut a framework member 52. In some embodiments, movement of the element applies a compressive stress to framework members 52 or relieves a compressive strain. In various embodiments, pulleys or gears may also be employed to move movable portions. For example, movable portions may ride along a track defined along the elongate member 18. The track may include gears configured to move a movable portion or adjust a length of the elongate member 18 between movable portions, for example, by nesting a portion of the elongate member 18.

Figure 12:
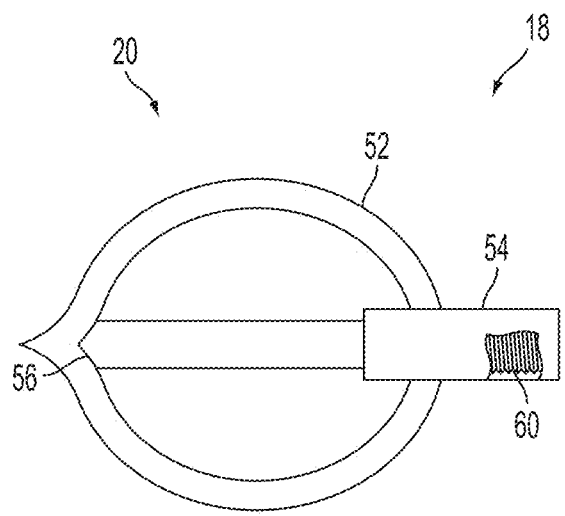
FIG. 12 illustrates an expandable portion in an expanded state according to certain embodiments described herein.

In various embodiments, framework members 52 may be movable with respect to the elongate member 18. One or more framework members 52 or portions thereof may be configured to slide along or pivot with respect to the elongate member 18. For example, a first portion of a framework member 52 may be fixed or pivotably fixed to the elongate member 18 at a first position and a second portion of the framework member 52 may be fixed or pivotably fixed to the elongate member 18 at a second position. FIG. 12 illustrates an embodiment of an expandable portion 20 in an expanded state. The expandable portion 20 comprises a plurality of longitudinal framework members 52 disposed along a distal portion of the elongate member 18. For simplicity, only two longitudinal framework members 52 are illustrated. The longitudinal framework members 52 extend along the axis between a proximal movable portion comprising a proximal coupler 54 and at distal coupler 56 adjacent to the tip 28. The proximal coupler 54 comprises a rotatable portion rotatably movable along the elongate member 18 upon threads 60 provided about the elongate member 18. Rotation of the proximal coupler 54 in a first direction moves the proximal coupler 54 proximally and rotation of the proximal coupler 54 in a second direction moves the proximal coupler 54 distally. Proximal and distal movement of the proximal coupler 54 corresponds to a relative movement between the proximal coupler 54 and the distal coupler 56. In one embodiment, when the proximal coupler 54 moves distally, the distance between the proximal coupler 54 and the distal coupler 56 decreases and a compressive stress is applied to the longitudinal framework members 52. The compressive stress causes a deformative strain marked by bowing of the longitudinal framework members 52 outward of the axis, thus, increasing a diameter of the expandable portion 20. Alternately, when the proximal coupler 54 moves proximally, the distance between the proximal coupler 54 and the distal coupler 56 increases and the compressive stress is relieved. Relief of the compressive stress allows the longitudinal framework 52 members to relax inward and longitudinally align along the axis, thus, decreasing a diameter of the expandable portion 20. In another embodiment, a proximal movement of the proximal coupler 54 applies a tension stress to the longitudinal framework members 52 resulting in a deformative strain marked by inward positioning of longitudinal framework members 52 decreasing a diameter of the expandable portion 20. Alternately, a distal movement of the proximal coupler 54 relieves the tension stress allowing longitudinal framework members 52 to relax outward of the axis, thus, increasing the diameter of the expandable portion 20. In some embodiments, the compressive stress comprises a retaining force and the proximal coupler 54 comprises a retaining structure. Thus, in a memory form, longitudinal framework members 52 may extend inward or bow outward of the axis, and, in the retained form, longitudinal framework members 52 may be compressed to bow outward of the axis or tensioned to straighten and radially align inward toward the axis. In some embodiments, framework members 52 do not rotate corresponding to rotation of a proximal or distal coupler 56. For example, couplers may comprise abutment surfaces configured to compress a first portion of a framework member 52 against or relative to a second portion of a framework member 52. In certain embodiments, couplers may comprise a track upon which a first portion of framework member 52 may maintain axial positioning relative to a second portion of the framework member 52. Similarly, couplers may comprise a sleeve upon which a first portion of a framework member 52 is coupled. The sleeve may be rotatable about an inner portion of the coupler upon bearings such that the first portion of the framework member 52 may maintain axial positioning corresponding to movements of the inner portion of the coupler.

It is to be appreciated that the proximal and distal orientation is provided to assist in the understanding of the systems, devices, and methods disclosed herein. In certain embodiments orientations and/or arrangements may be reversed such that the goal of transitioning an expandable portion remains that same. For example, the distal coupler 56 may be rotatably movable upon threads, for instance, provided near the distal coupler 56. Such orientational variations do not deviate from this disclosure. Indeed, in one embodiment, the proximal coupler 54 and the distal coupler 56 are rotatable about threads provided about the surface of the elongate member 18. Similarly, in another embodiment, the distal coupler 56 is clickably movable along the elongate member 18. In further embodiments, a series of framework 50 arrangements and/or expandable portions 20 may be disposed along the distal portion of the elongate member 18. Such a series of framework 50 arrangements and/or expandable portions 20 may be configured for a desired application and provide customizable ablation zones within a biological lumen or treatment site.

Figure 13:
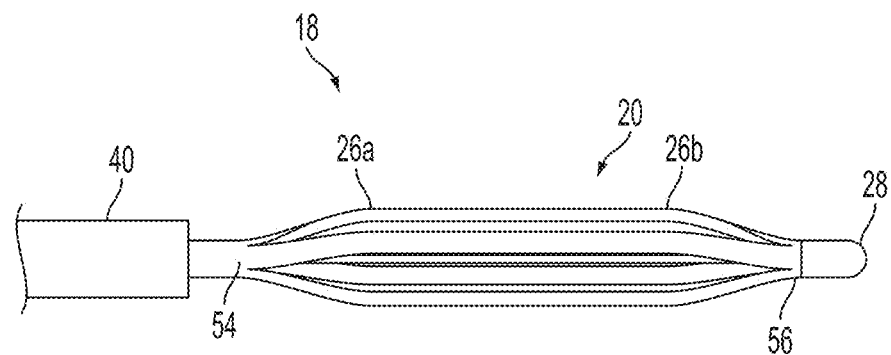
FIG. 13 illustrates an expandable portion transitioning from a contracted state to an expanded state according to certain embodiments described herein.
Figure 14:
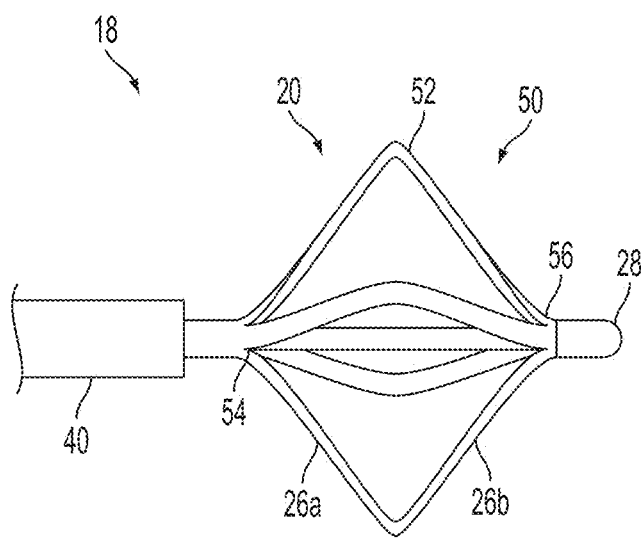
FIG. 14 illustrates the expandable portion illustrated in FIG. 13 in an expanded state according to certain embodiments described herein.

FIG. 13 illustrates an embodiment of an expandable portion 20 comprising a four member basket. The framework members 52 are coupled at a proximal coupler 54 and a distal coupler 56. The proximal coupler 54 is movable relative to the distal coupler 56 such that a decrease in the distance between the couplers 54, 56 increases a diameter of the expandable portion 20, as shown in FIG. 14, and an increase in the distance between the couplers 54, 56 decreases the diameter of the expandable portion 20, as shown in FIG. 13. As shown in FIG. 14, in the expanded state, framework members 52 have a proximal tapered portion 26a and a distal tapered portion 26b defining an interior angle of about 80°. In some embodiments, the degree of expansion is a function of the lengths 26a,b and the angle defined therebetween. For example, increasing a length 26a,b may increase degree of expansion and decreasing the angle defined between the lengths 26a,b may increase degree of expansion. In some embodiments, a portion of the elongate member 18 may be translatable through the proximal coupler 54 and fixed relative to the distal coupler 56 such that retracting the elongate member 18 relative to the proximal coupler 54 decreases the distance between the proximal coupler 54 and the distal coupler 56 and advancing the elongate member 18 relative to the proximal coupler 54 increases the distance between the proximal coupler 54 and the distal coupler 56. Accordingly, when the elongate member 18 is withdrawn proximally, the distal coupler 56 moves proximally and framework members 52 compress and bow outward in a retained form corresponding to an expanded state of the expandable portion 20. Similarly, framework members 52 may comprise a memory form corresponding to an expanded state of the expandable portion 20 such that when the elongate member 18 is withdrawn proximally, the distal coupler 56 moves proximally and framework members 52 tense and straighten inward in a retained form corresponding to a contracted state of the expandable portion 20. Compression of the framework members 52, as illustrated in FIG. 14, may result in radial bowing of the framework members 52 outward of the axis, increasing a diameter of the expandable portion 20. Depending on the desired application, numerous configurations of a plurality of framework members 52 arranged along an axis may be configured to flex, bend, deform, or otherwise strain in response to stress. For example, framework members 52 may be configured to flex, bend, deform, or otherwise strain at two or more positions, thus forming a basket similar to that which is depicted in FIG. 9. In some embodiments, 5, 6, 8, 15, or more framework members 52 may be provided that flex, bend, deform, or otherwise strain along a plurality of positions and, for example, take on a spherical shape in the expanded state.

Figure 15:
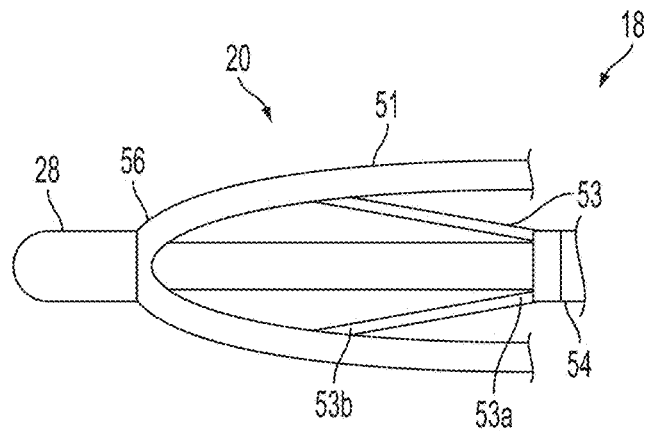
FIG. 15 illustrates an expandable portion transitioning from a contracted state to an expanded state according to certain embodiments described herein.
Figure 16:
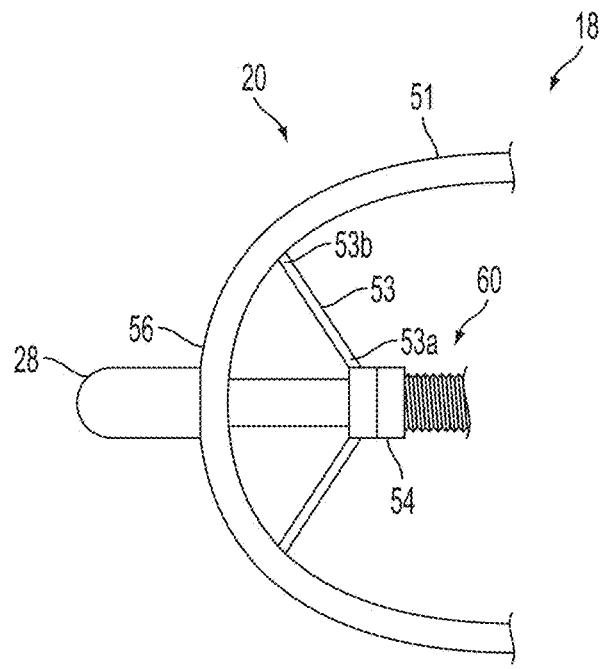
FIG. 16 illustrates the expandable portion illustrated in FIG. 15 in an expanded state according to certain embodiments described herein.
Figure 17:
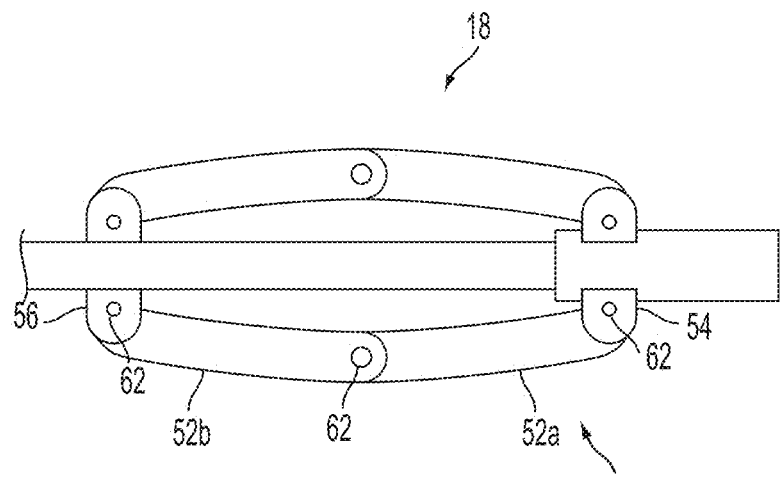
FIG. 17 illustrates an expandable portion transitioning from a contracted state to an expanded state according to certain embodiments described herein.

FIG. 15 illustrates yet another embodiment of an expandable portion 20. In this embodiment, relative movements between framework members 52 expand the expandable portion 20 similar to an umbrella. In particular, one or more framework members 52 comprising extenders 53 are provided. First ends 53a of the extenders 53 are pivotably coupled to a proximal coupler 54 positionable along a length of the elongate member 18. Second ends 53b of the extenders 53 are pivotably coupled to one or more additional framework members comprising ribs 51. Ribs 51 may comprise a flexible material (e.g., an elastic, series of jointed framework members, or a portion of a flexible covering) or, in some embodiments, a rigid material and may be fixedly coupled to the elongate member 18 at a distal coupler 56 adjacent to the distal tip 28 such that extension of extenders 53 extend portions of the ribs 51 outward of the axis. The extenders 53 are preferably sufficiently rigid to extend ribs 51 by, for example, bending, flexing, or swinging the ribs 51 outward of the axis. In the illustrated embodiment, a transition between the contracted state and an expanded state comprises a relative movement between the proximal 54 and distal 56 couplers. For example, a transition from the contracted state to an expanded state comprises decreasing the distance between the couplers 54, 56. A relative movement between couplers 54, 56 may be accomplished in any suitable manner. For example, in one embodiment a clinician may distally reposition the proximal coupler 54 by proximally pulling a nested portion of the elongate member 18 comprising the distal coupler 56 using an actuator provided on the handle (not shown). FIG. 16 illustrates an embodiment of the expandable portion 20 depicted in FIG. 15 in an expanded state. As can be seen, the extenders 53 prop and extend the ribs 51 outward of the axis in response to a relative movement between the proximal 54 and distal 56 couplers. In this embodiment, the proximal coupler 54 includes a rotatable portion rotatable upon threads 60 provided about an adjacent surface of the elongate member 18. Extenders 53 are extendable by distally rotating the proximal coupler 54 and retractable by proximally rotating the proximal coupler 54. In various embodiments, the proximal coupler 54 is repositionable by proximally or distally sliding the coupler 52 along the elongate member 18. In additional embodiments, second or third extenders may be associated with first extenders 53. For example, second extenders may comprise a first end pivotably coupled to a central portion of a first extender and a second end pivotably coupled to an additional framework member, such as a rib 51. Third extenders may be similarly configured. Second and third extenders may provide additional structure and or support to expandable portions 20 or increase expansion. In other embodiments, an extender 53 may be a wedge having an engagement surface configured to engage and prop up a rib 51. For example, as the distance between the wedge and the distal coupler 56 decreases, the wedge progressively moves along the underside of the rib 51, swinging the rib 51 outward of the axis, and expanding a diameter of the expandable portion 20.

Figure 18:
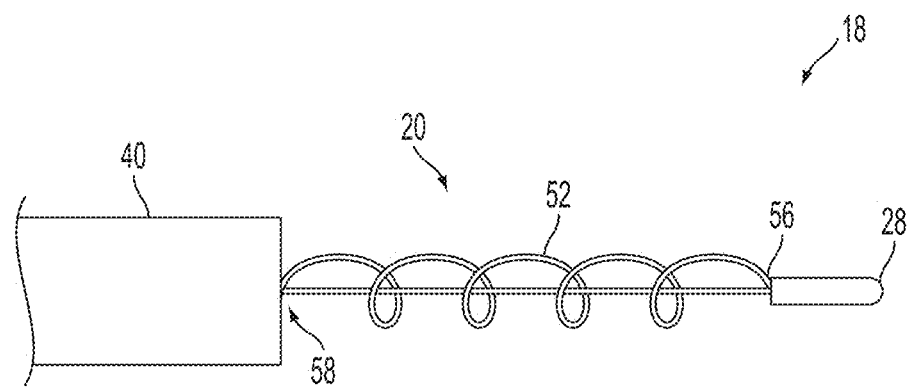
FIG. 18 illustrates a deployed expandable portion in a contracted state according to certain embodiments described herein.

FIG. 18 illustrates yet an additional embodiment of an expandable portion 20 comprising two pivotably coupled framework members 52a,b. The expandable portion 20 is illustrated in a slightly expanded state. The framework members 52a,b are pivotably coupled about a joint 62 (e.g., a hinge, pin, or flexible portion) at adjacent ends. Each framework member 52a,b is pivotably coupled to the elongate member 18 about additional joints 62 at respective proximal 54 and distal couplers 56. The proximal 54 and distal couplers 56 are relatively movable with respect to each other. In this embodiment, transitioning the expandable portion 20 from the contracted state to the expanded state comprises relatively moving the proximal 54 and distal couplers 56 and comprises nesting an intervening portion of the elongate member 18. For example, nesting the distal portion within the proximal portion of the elongate member 18 decreases the distance between the proximal 54 and distal couplers 56, resulting in an outward pivoting of the adjacent ends of the framework members 52a,b, increasing a diameter of the expandable portion 20, and thereby expanding the expandable portion 20. Conversely, unnesting the distal portion from the proximal portion increases the distance between the proximal 54 and distal couplers 56, resulting in an inward pivoting of the adjacent ends of the framework members 52a,b, decreasing the diameter of the expandable portion 20, and thereby contracting the expandable portion 20. For simplicity, FIG. 18 includes only two coupled framework members 52a,b; however, additional framework members may similarly be coupled to the framework members 52a,b. For example, a third framework member may be coupled between the two framework members 52a,b illustrated in FIG. 18 such that a relative movement between the proximal 54 and distal couplers 56 extends the third framework member outward of the axis relatively parallel with the axis. Also for simplicity, FIG. 18 includes only two sets of coupled framework members 52a,b; in additional embodiments, three or more sets of coupled framework members 52a,b are provided about the circumference of the elongate member 18 to further increase the diameter of the expandable portion 20 in the expanded state.

In certain embodiments, framework members 52 may comprise a coil operatively coupled to the elongate member 18 at a first position. In such an embodiment, relative counter rotation between the first position and a second position at least partially unwinds the coil and corresponds to an increase in a diameter of the expandable portion 20. For example, when the framework member 52 is a right-handed coil or helix a clockwise rotation of a proximal position relative to a distal position transitions the expandable portion 20 between the contracted state and an expanded state while a counterclockwise rotation of the proximal position relative to the distal position transitions the expandable portion 20 from an expanded state to the contracted state. Similarly, when the framework member 52 is a left-handed coil or helix a clockwise rotation of the distal position relative to the proximal position transitions the expandable portion 20 from the contracted state to an expanded state while a counterclockwise rotation of the distal position relative to the proximal position transitions the expandable portion 20 from an expanded state to a more contracted state. In a similar embodiment, the longitudinal distance between the proximal and distal positions is also adjustable. For example, the proximal position may be slidable toward the distal position, thus, reducing the distance between the two. In one embodiment, one or both positions are threadably rotatable about the elongate member 18 such that rotation of the positions increases or decreases the distance between the proximal and distal positions. In other embodiments, one or both positions are clickably or slidably positionable along the elongate member 18. It is to be appreciated that a coil may be rotatable at multiple positions such that various diameters along the length of the expandable portion 20 may be adjustable to meet various applications.

Figure 19:
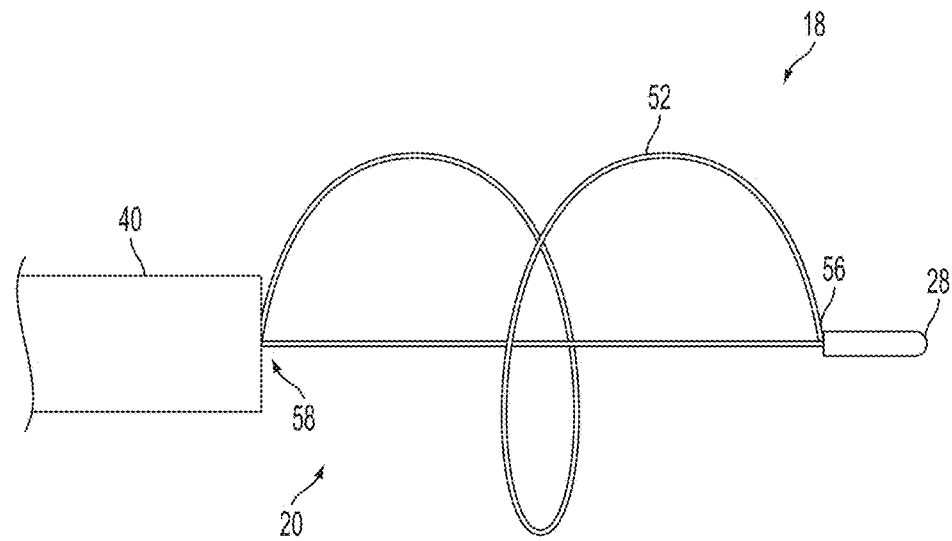
FIG. 19 illustrates the expandable portion illustrated in FIG. 18 in an expanded state according to certain embodiments described herein.
Figure 20:
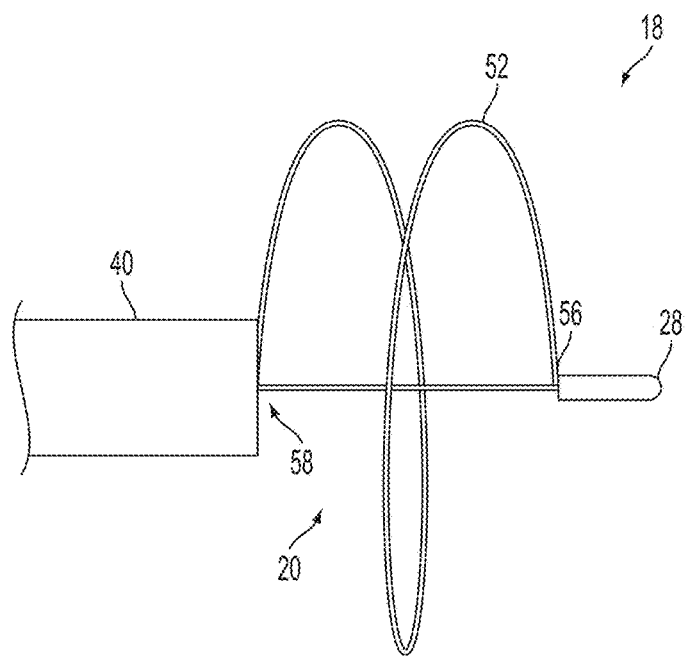
FIG. 20 illustrates an additional embodiment of the expandable portion illustrated in FIG. 18 in an expanded state according to certain embodiments described herein.

FIG. 18 illustrates an embodiment of an expandable portion 20 in the contracted state comprising a coiled framework member 52. The coil is coupled to the elongate member 18 at a distal coupler 56 adjacent to a distal tip 28 such that a transition of the expandable portion 20 from the contracted state to an expanded state comprises a counter rotation between the distal coupler 56 and a proximal position 58 of the framework member 52, as illustrated in FIG. 19. It is to be appreciated that the coil may be proximally coupled or fixed relative to the sheath 40 or otherwise proximally independent of a rotation of the distal coupler 56. FIG. 19 illustrates an embodiment of the expandable portion 20 shown in FIG. 18 in the expanded state following multiple clockwise rotations of the distal coupler 56 relative to the proximal portion 58 of the coil. According to this embodiment, counterclockwise rotation of the distal coupler 56 relative to the proximal portion 58 of the coil transitions the expandable portion 20 from an expanded state to a less contracted state. FIG. 20 illustrates a further embodiment of the expandable portion 20 depicted in FIGS. 18 and 19 and includes a method of further increasing the degree of expansion of the expandable portion 20 by decreasing its length. For example, a clinician may withdraw a portion of the elongate member 18 within the sheath 40 while maintaining the length of framework member 52 deployed from its distal end. In this way, the expandable dimension may be further customized to fit any one of a number of desired applications.

Figure 21:
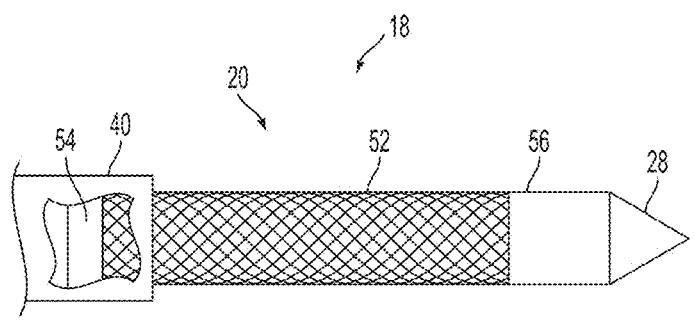
FIG. 21 illustrates an expandable portion partially deployed and in a contracted state according to certain embodiments described herein.
Figure 22:
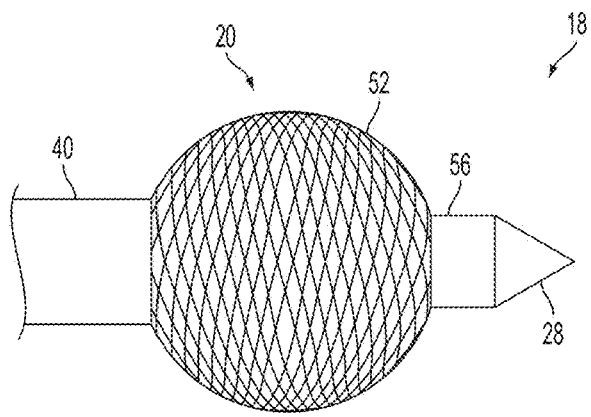
FIG. 22 illustrates the expandable portion illustrated in FIG. 21 in an expanded state according to certain embodiments described herein.

FIG. 21 illustrates an expandable portion 20 comprising a framework member 52 orientated in a tube-like braid extending along a distal portion of a elongate member 18. The expandable portion 20 is illustrated in a partially deployed position and is in a contracted state. A proximal end of the braid is coupled to a proximal coupler 54 (shown in cutaway). A distal end of the braid is coupled to a distal coupler 56 adjacent to a distal tip 28. In this embodiment, relative movement between the proximal coupler 54 and the distal coupler 56 transitions the expandable portion 20 between the contracted state and an expanded state. Notably, in some embodiments, a sheath 40 may be provided that may, in certain instances, at least partially be utilized as a proximal coupler 54. For example, as illustrated in FIG. 22, when the distal coupler 56 moves proximally with respect to the proximal coupler 54, the braid is compressed. The braid orientation of the framework member 52 also enables loosening of the braid such that the distance between individual overlaps of framework members 52 within the braid increases in response to compressive stress. Because the length of deployed braid does not decrease to the extent of the relative movement between the proximal coupler 54 and the distal coupler 56, a dimension, or in this instance, a diameter, of the expandable portion 20 increases. Alternatively, when relative movement between the proximal coupler 54 and the distal coupler 56 results in an increase in the distance between the respective couplers 54, 56, tension on the framework members 52 decompresses the braid, decreasing a diameter of the expandable portion 20 to a less expanded state. In some embodiments, a full transition from an expanded state to a contracted state comprises relative movement between the proximal coupler 54 and the distal coupler 56 increasing the distance between the two couplers such that the tension stress applied to the braid is sufficient to contract the braid to a predetermined diameter.

Figure 23:
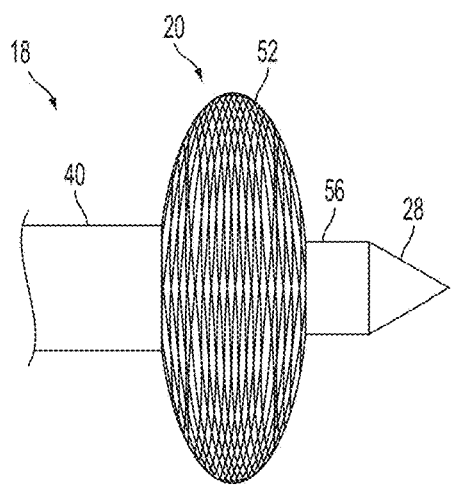
FIG. 23 illustrates an additional embodiment of the expandable portion illustrated in FIG. 21 and FIG. 22 in an expanded state according to certain embodiments described herein.

FIG. 23 illustrates a further embodiment of the expandable portions 20 illustrated in FIGS. 21 and 22 that includes an additional feature to customize the degree of expansion. In this embodiment, a clinician may selectively control or choose the degree to which the expandable portion 20 expands by adjusting the distance between the proximal coupler 54 and the distal coupler 54. As can be seen, a decrease in distance between the coupler 54, 56 increases a diameter of the expandable portion 20 while an increase in the distance between the couplers 54, 56 decreases the diameter. In this way, a clinician may beneficially control the diameter of the expandable portion 20. Furthermore, when a sheath 40 is provided that may be at least partially utilized as a proximal coupler 54, a clinician may compensate for a decrease in length of the deployed expandable portion 20 by deploying additional expandable portion 20 (such as framework members 52) that may also be compressed to increase the diameter of the expandable portion 20.

As previously described, one or a multiple of methods may be employed to effectuate a relative movement between a first movable portion comprising a proximal portion of framework members 50, such as a proximal coupler, and a second movable portion comprising a distal portion of framework members 52, such as a distal coupler. For example, in some embodiments, a clinician may engage an interface to signal actuation or a relative movement between the first and second portions. Actuation signals may trigger transitions effectuated by mechanical and/or electrical elements. In certain embodiments, an actuator comprises a manipulator configured to manually extend or retract portions of framework members 52 and/or portions of the elongate member 18. A signal may result in a rotation of a coupler about a threaded track, as in FIG. 12, for example, or a slide of the first movable portion relative to the second movable portion, as in, FIG. 14, for example. The elongate member 18 may additionally be fitted with longitudinal tracks or rails in which the first and/or second movable portions may transition. In some embodiments, an intervening span of elongate member 18 between the first and second movable portions may decrease in length by telescopically nesting or folding into an adjacent span, as in, for example, FIG. 17. Such a decrease in length of an intervening span of elongate member 18 may be aided by a bias configured to releasably extend or retract the intervening span. In certain embodiments, framework members 52 and/or the elongate member 18 may be fitted with gears configured to relatively move portions thereof.

Figure 24:
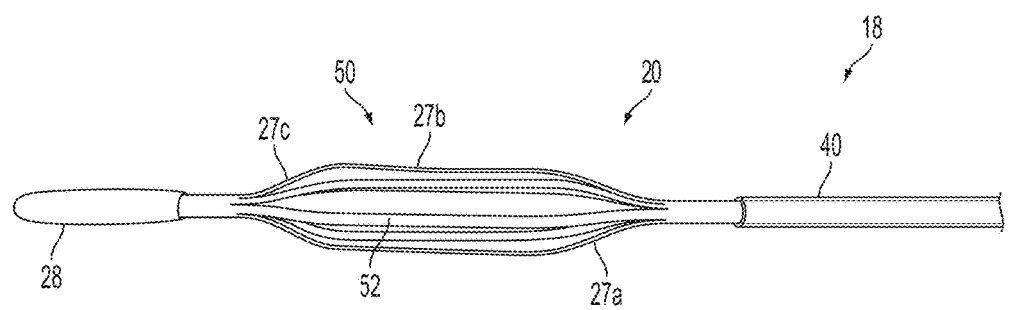
FIG. 24 illustrates an expandable portion in an expanded state according to certain embodiments described herein.

FIG. 24 illustrates an expandable portion 20 in an expanded state according to various embodiments. The expandable portion 20 comprises a plurality of framework member 52 comprising a thermoresponsive shape memory material defining a basket. The framework members 52 extend along the axis and each comprise a linear portion 27b flanked by a distal tapered portion 27c and proximal tapered portion 27a. As shown, the proximal tapered portion 27a of each framework member 52 diverges away from the axis at a first angle, and the distal tapered portion 27c of each framework member 52 converges toward the axis at a second angle. As can be seen, the degree of expansion is a function of the lengths of the tapered portions 27a,c and their degree of divergence away and convergence toward the axis. For example, increasing the length of the tapered portions 27a,c increases the diameter of the expandable portion 20. Additionally, the degree of expansion increases as the degree of divergence and convergence approaches 90°. In some embodiments, such an expansion in diameter is also accompanied by a reduction in length of the expandable portion 20. When the expandable portion 20 is in the contracted state, as illustrated in FIG. 25, proximal tapered portions 27a, linear portions 27b, and distal tapered portions 27c extend relatively linearly along the axis such that the expandable portion 20 may be received by a channel defined within the sheath 40.

Figure 25:
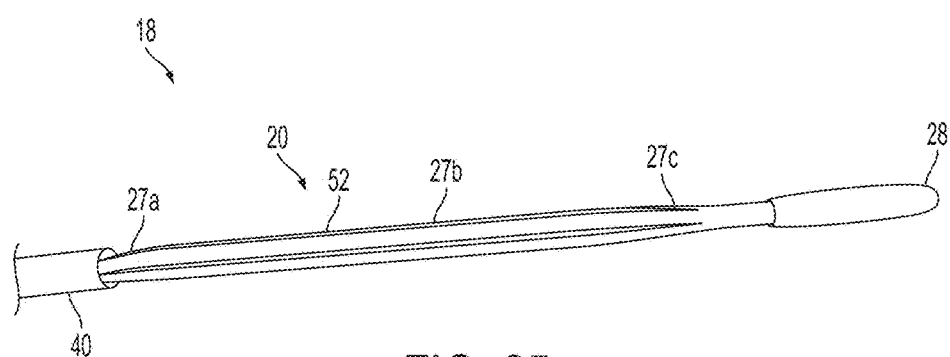
FIG. 25 illustrates the expandable portion illustrated in FIG. 24 in a contracted state according to certain embodiments described herein.

In the embodiment illustrated in FIGS. 24 and 25, framework members 52 exhibit two-way memory. That is, framework members 52 comprise at least two memory forms and are transitional between the at least two memory forms in response changes in temperature. At temperatures at or below a low transition temperature, framework members 52 are in a low temperature form. At temperatures at or above a high transition temperature, framework members 52 are in a high temperature form. Depending on desired application, the low temperature form may correspond to either the expanded state or the contracted state and the high temperature form may correspond to either the expanded state or contracted state. A clinician may signal a transition comprising a temperature change through an actuator located on the handle (not shown). Actuation may result in transmission of energy, such as vibrations, to the framework members 52 sufficient to increase the temperature of framework members 52 and effectuate a transition to the high temperature form. Actuation may also comprise deployment into a biological environment, in some embodiments. For example, a transition temperature may be set at or below a biological temperature such that when framework members 52 are exposed to biological temperatures, the expandable portion 20 undergoes a transition.

Figure 26:
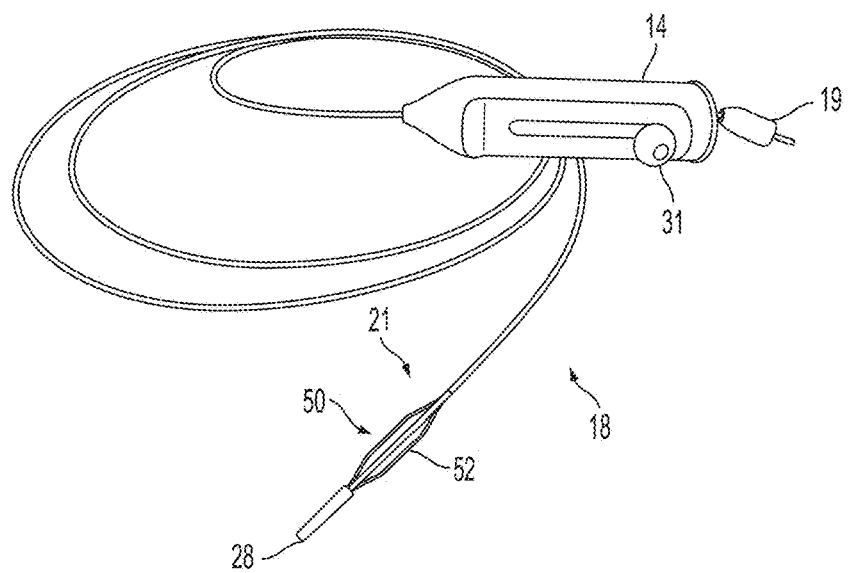
FIG. 26 illustrates an electrical ablation device comprising a handle and an elongate member according to certain embodiments described herein.

In some embodiments, a sheath 40 is not provided and an electrode 21 may be delivered to a target region within another delivery device. In some such embodiments, the electrode 21 may be delivered to the target region naked, that is, not within an artificial channel. In these and other embodiments, the electrode 21 may be delivered to a target region by advancing the elongate member 18 through a biological orifice or lumen. Once delivered to the target region, the electrode 21 may be expanded in response to an actuation signal. The electrical ablation device 12 illustrated in FIG. 26 is configured for use and delivery to a target region either within an artificial delivery channel or naked. The device 12 includes a handle 14 through which a conductive elongate member 18 extends. Near the proximal end of the handle 14, the elongate member 18 comprises a connector 19 for connecting the elongate member 18 to a power source (not shown). The elongate member 18 extends distally from the distal end of the handle 14 and includes an electrode 21 disposed along a distal portion of its length and a distal tip 28. The electrode 21 comprises an expandable portion 20 comprising a plurality of framework members 52 arranged in a basket similar to the embodiment depicted in FIG. 24. The handle 14 comprises an actuator 31 configured to transition the expandable portion 20 between contracted and expanded states by any suitable method.

In various embodiments, the elongate member 18 may be flexible along all or a portion of its length. Such flexible portions may be bendable, deformable, or elastic, for example. Flexible portions may also be conditionally flexible or conditionally rigid. In some embodiments, the elongate member 18 comprises flexible portions which may be mechanically bendable such that portions of the elongate member 18 are pivotable in response to a signal or otherwise manipulable. In one embodiment, the elongate member 18 comprises a maneuverable portion configured to maneuver within a biological lumen such as vascular, duct, cavity, orifice, or tract area, for example, and deliver an electrode 21, to a target site. In one embodiment, a cardiac catheter platform comprises one or more electrodes 21 disposed along the distal portion of a flexible and/or maneuverable elongate member 18 configured to deliver the one or more electrodes 21 into chamber, vessel, or a surface of the heart to endocardially ablate spots for treatment for atrial fibrillation, for example. The one or more electrodes 21 may be selectively expandable between contracted and expanded states. In some embodiments, multiple electrodes 21 are disposed along the distal portion of the elongate member 18 and spaced to deliver energy to cardiac tissue within a tightly controlled electric field. In some such embodiments, the distance between electrodes 21 along the distal portion of the elongate member 18 may be adjustable to conform to a particular procedure.

Figure 27:
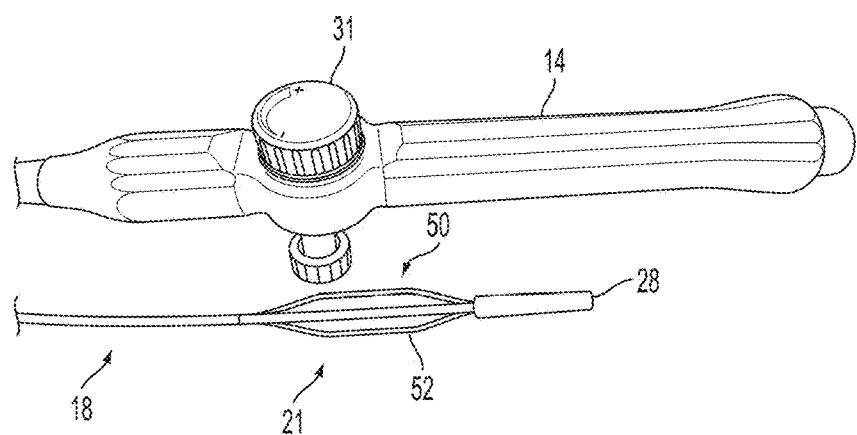
FIG. 27 illustrates an electrical ablation device comprising a handle and an elongate member according to certain embodiments described herein.

Referring to FIG. 27, a cardiac catheter platform according to various embodiments is illustrated. The platform comprises a catheter assembly comprising an electrode 21 disposed along a distal portion of an elongate member 18. The platform further comprises a handle 14 configured to maneuver the elongate member 18 and electrode 21 under imaging into the heart to endocardially ablate spots or points as a treatment for atrial fibrillation. In the illustrated embodiment, the elongate member 18 is equipped with a long insulated tip 28 located at the distal end of the elongate member 18. The tip 28 may be configured to beneficially increase the ability of a clinician to thread, steer, or navigate the elongate member 18 and electrode 21 to a tissue treatment region. In various embodiments, a cardiac catheter platform may comprise an expandable portion 20 comprising a comparatively increased length over certain other embodiments. An increased length may be advantageous in certain treatment applications by allowing a clinician to more easily connect ablative points along a desired lesion line. In some embodiments, an expandable portion 20 comprising an adjustable length, as previously described, may be provided to customize the expandable portion 20 to flexibly suit particular surgical applications. In some embodiments, the length may be conveniently adjusted at or near the tissue treatment site. Such a feature may beneficially decrease treatment time by enabling a clinician to adjust the expanded length of the electrode 21 to adaptively connect ablative points during a procedure without a need to completely remove the catheter. Referring again to FIG. 27, a system comprising the illustrated cardiac catheter may further comprise a second electrode 22 (not shown) configured to couple to an energy source (not shown). The second electrode 22 may be a return pad, needle, clamp, second probe, or second electrode disposed along the distal portion of the elongate member 18.

FIG. 28A includes a photograph of an ablation zone following ablative treatment according to various embodiments. Using intravascular approaches described herein, an electrode 21 was placed in a porcine liver duct and a second electrode 22 comprising a return was placed on the skin. As can be seen, following ablative treatment, an ablation zone 80 surrounded the vessel. No lesions or burns were observed at the tissue around the site of the return. FIG. 28B includes a photograph of an ablation zone 80 following ablative treatment according to various embodiments. Using intravascular approaches described herein an electrode 21 was placed in a porcine liver vessel and a second needle electrode 22 was placed into the liver parenchyma. As can be seen, following ablative treatment, an ablation zone 80 surrounded the vessel. FIG. 29 includes a photograph of an endocardiac ablation zone 80 following ablative treatment according to various embodiments. Using intravascular approaches described herein, an electrode 21 was contacted with porcine heart tissue. Following ablative treatment, an ablation zone 80 comprising a lesion line along cardiac tissue was observed.

In various embodiments, electrical ablation devices 12 include accessory features such as optics, applicators, and sensors. For example, transducers or sensors may be located in the handle 14, or tip 28, or other suitable location to sense, for example, the force required to expand an electrode 21. This feedback information may be useful to determine whether electrodes 21 have been properly positioned within a biological lumen at or near a tissue treatment site. Manual actuation of an expandable portion 20 may similarly provide feedback to a clinician regarding the force required to fully expand the expandable portion 20. In this way, the clinician may decide that full expansion of the expandable portion 20 is either unnecessary or may otherwise result in unnecessary trauma and adjust the degree of expansion accordingly. In certain embodiments, feedback is provided to the clinician to physically sense when an electrode 21 is placed at or near a tissue treatment site. In some embodiments, feedback information provided by the transducers or sensors may be processed and displayed by circuits located either internally or externally to the energy source 11. Sensor readings may be employed, for example, to determine whether an electrode 21 has been properly located at or near a tissue treatment site thereby assuring a suitable margin of error has been achieved in locating the electrode 21. Sensor readings may also be employed, for example, to determine whether pulse parameters need to be adjusted to achieve a desired result, such as, for example, reducing the intensity of muscular contractions in the patient.

In one embodiment, an electrical ablation device 12 includes an accessory feature comprising an electrolyte applicator. An electrolyte applicator may be configured to apply or deliver an exogenous electrolyte at or near a tissue treatment site. An electrolyte applicator may include a delivery portion and a reservoir portion. In some instances, the delivery portion may comprise the reservoir portion. The reservoir portion may be configured to contain electrolyte for delivery. The delivery portion may be configured to deliver electrolyte at or near the tissue treatment site. In some embodiments, the delivery portion comprises a channel adjacent to or within the elongate member 18 or sheath 40. In one embodiment, the delivery portion comprises the tip 28. A clinician may actuate an actuator located on the handle 14, for example, to deliver electrolyte from the delivery portion. In certain embodiments, the delivery portion may be deployable independent of the electrode 21 from a lumen or artificial channel. In some embodiments, the delivery portion, reservoir portion, or the electrolyte applicator may be separate from the electrical ablation system 10. In various embodiments, the delivery portion of an electrolyte applicator may apply an aqueous electrolyte solution to the treatment area prior to or during a treatment to increase conductivity. In other embodiments, however, no solution may be added or a separate or same accessory feature may be configured to apply suction to a treatment area to, for example, remove fluids prior to or during a treatment.

In certain embodiments, at least one of a temperature sensor and pressure sensor may be located in or proximate the electrical ablation system 10. The temperature sensor and/or pressure sensor may be located within the handle 14, protective sleeve 38, sheath 40, elongate member 18, at the distal end of the elongate member 18, such as the tip 28, or within one or more electrodes 21. In certain embodiments, the temperature sensor and/or pressure sensor may be separate from the electrical ablation system 10. The temperature sensor and pressure sensor may provide feedback to the operator, surgeon, or clinician to apply an electric field pulse to the undesirable tissue. The pressure and/or temperature information may be useful to determine whether the undesirable tissue may be treated having reduced or no detrimental thermal effects to surrounding healthy tissue. According to certain embodiments, the temperature sensor may measure the temperature of the tissue treatment region, undesirable tissue, or the area surrounding one or more electrodes before, during, and/or after treatment such as before and/or after the first and/or second sequences of electrical pulses are delivered to the tissue. According to certain embodiments, the pressure sensor may measure the pressure of the tissue treatment region, the space between the electrodes, and/or the area surrounding one or more electrodes before, during, and/or after treatment, such as before and/or after the first and/or second sequences of electrical pulses are delivered to the tissue.

The electrical ablation system 10 may be employed to ablate undesirable tissue in delicate zones or near critical structures and be deployed through a biological lumen, such as vascular, ducts, or tract areas. The electrical ablation system 10 may be configured to treat a number of lesions and osteopathologies comprising metastatic lesions, tumors, fractures, infected sites, and inflamed sites in a tissue treatment region using electrical energy. The electrical ablation devices 12 may be configured to be positioned within a patient's natural body orifice, e.g., the mouth, anus, and vagina, and/or advanced through internal body lumen or cavities, e.g., the esophagus, stomach, intestines, colon, cervix, and urethra, to reach the tissue treatment region. For example, an elongate member 18 may be configured to be positioned and passed through a small incision or keyhole formed through the patient's skin or abdominal wall using a trocar to reach the tissue treatment region. The tissue treatment region may be located in the patient's brain, lung, breast, liver, gall bladder, pancreas, prostate gland, various internal body lumen defined by the esophagus, stomach, intestine, colon, arteries, veins, anus, vagina, cervix, fallopian tubes, and the peritoneal cavity. The electrical ablation system 10 may be used in conjunction with endoscopic, laparoscopic, thoracoscopic, open surgical procedures via small incisions or keyholes, percutaneous techniques, transcutaneous techniques, and/or external non-invasive techniques, and any combinations thereof.

In one embodiment, the electrical ablation device 12 may be employed in conjunction with an artificial channel (e.g., a flexible endoscope, as well as a rigid endoscope, laparoscope, or thoracoscope, such as the GIF-100 model available from Olympus Corporation). In one embodiment, the endoscope may be introduced to the tissue treatment region trans-anally through the colon, trans-orally through the esophagus and stomach, trans-vaginally through the cervix, transcutaneously, or via an external incision or keyhole formed in the abdomen in conjunction with a trocar. The electrode 21 may thereby be delivered to a tissue treatment region via insertion and guided into or proximate the tissue treatment region using the endoscope. Such delivery may also be accomplished using other various artificial channels. The endoscope or other artificial channel may define one or more channels for receiving additional devices such as a light source and a viewing port. Images within the field of view of the viewing port may be received by an optical device, such as, for example, a camera comprising a charge coupled device (CCD) usually located within the endoscope, and transmitted to a display monitor (not shown) outside the patient. In other embodiments, the endoscope is not utilized, and the electrical ablation device 12 comprises a light source and/or a viewing port, for example. Still additional embodiments employ other techniques to determine proper instrument placement, such as, for example, ultrasound or a computerized tomography (CT) scan.

According to one embodiment, methods of electrically ablating tissue include delivering a first electrode 21 to a tissue treatment region. The first electrode 21 may be configured to couple to the energy source and to a tissue treatment region located within or near a lumen. In one embodiment the first electrode 21 is delivered or directed into a lumen at or near a tissue treatment region through a hollow bore, such as an artificial channel. The first electrode 21 may then be deployed at or near a tissue treatment site. Once deployed, an expandable portion 20 of the first electrode 21 may be expanded in at least one dimension (e.g., diameter or length) and then contacted with the lumen wall. A second electrode 22 may be coupled to the first electrode 21 and the patient such that the second electrode 22 is in conductive communication with the first electrode 21 through the patient and represents a difference in electric potential with respect to the first electrode 21. For example, in some embodiments, the second electrode 22 may be a ground or return pad, a needle electrode, or medical clamp in contact or conductive communication with the patient. In various embodiments, the second electrode 22 may be a separately placed electrode, such as a conductive material, return pad, needle, or clamp, for example, may be located at a near by or adjacent tissue, surface, or lumen. Once delivered to a tissue treatment region, the first electrode 21 may be actuated (e.g., deployed, expanded, and energized) to ablate the undesirable tissue.

In some embodiments, expanding an expandable portion 20 of a first electrode 21 comprises transitioning the expandable portion 20 from a contracted state to an expanded state. Transitioning an electrode 21 from a contracted state to an expanded state may comprise increasing at least one dimension of the electrode 21. In certain embodiments, when the expandable portion 20 transitions from the contracted state to the expanded state, a diameter of the expandable portion 20 proportionally decreases in length. In other embodiments, however, the diameter of the expandable portion 20 does not expand proportionally to a decrease in length.

In some embodiments, the first electrode 21 may be alternately or selectively transitionable between a contracted state and an expanded state. In certain embodiments, a transition from a contracted state to an expanded state comprises a relative movement between two portions of a framework or framework members 52. The relative movement may be rotational or longitudinal. For example, a decrease in the distance between two portions of a framework 50 or framework members 52 may transition an expandable portion 20 from a contracted state to an expanded state. Relative movement may result in one or more framework members 52 extending outward of the axis. Outward extension may be the result of bowing of one or more framework members 52. Framework members 52 extending outward of the axis may similarly prop-up, extend, or otherwise reposition other framework members 52 outward of the axis. Various memory materials and orientations of framework members 52 may be employed to assist in transitioning an expandable portion 20 between contracted and expanded states. For example, framework members 52 may be arranged as springs, coils, braids, multi-member baskets, umbrellas, and injectable cavities and may comprise rigid, jointed, or memory materials, including shape set memory superelastics. For example, framework members 52 may comprise metallics, alloys, rubbers, plastics, polymers, and various conductive materials.

In various embodiments, expanding an electrode comprises expanding a diameter or radius or of the expandable portion many times that of the electrode in a contracted state. Depending on the desired application, electrodes may expand 2, 5, 10, 20, 40 or more times in diameter or radius to expand to a diameter conforming to a diameter of a tissue treatment region comprising a biological lumen, such as, for example, a larynx. In various embodiments, the diameter of the first electrode may by different from the diameter of the second electrode. Similarly, in some embodiments, the first electrode may have a different length than the second electrode. Again, depending on the desired application, such variations are contemplated and are considered within this disclosure. As is to be appreciated, when multiple electrodes are disposed along the distal portion of an elongate member, various spacing between the electrodes may also be desirable. In some such embodiments, the distance from the first electrode to the second electrode may be adjusted from 0.5 cm to 3 cm, such as, for example, 1 cm, 1.5 cm, 2.0 cm, and 3 cm. However, in other applications it may be desirable to greatly increase the distance between first and second electrodes to, for example, customize the size of the electric field to a particular application.

Electrodes 21 may be introduced, delivered, deployed, or expanded according to any of the above methods and then contacted with a lumen wall. Contact with a lumen wall is preferably at least partially circumferential. Electrical current may then be applied in various pulse power outputs, such as monophasic square waves, biphasic square waves, RF modulated high voltage, or nanosecond duration pulses, for example. The applied current and waveform can be customized for the desired application and clinical goal to provide various tissue effects such as cell lysis, apoptosis, or irreversible electroporation.

FIG. 30 is a representative use of an electrical ablation system and device according to various embodiments. An elongate member 18 delivers the expandable portion 20 to a tissue region comprising a lumen 82 (e.g., a hepatic vein) employing methods herein disclosed. An alternate delivery placement of the elongate member 18' is additionally indicated by the dashed outline. The expandable portion 20 is then deployed from the distal end of the sheath 40 to the target site (e.g., a tumor surrounding the hepatic vein). Once deployed, the expandable portion 20 is expanded, e.g., transitioned from a contracted state to an expanded state. In FIG. 30, saline is introduced into the lumen to increase electrical conductivity prior to treatment (not shown). The expandable portion 20 is then contacted with a wall of the lumen and ablative treatment is applied. FIG. 30 illustrates an ablation zone 80 of ablated cells following such treatment. As can be seen in this depiction, in some embodiments, the dimensions of the expandable portion 20 in the lumen may determine the size of the zone.

Although the various embodiments of the devices have been described herein in connection with certain disclosed embodiments, many modifications and variations to those embodiments may be implemented. For example, different types of end effectors such as tips, electrodes, and elongate members may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. An electrical ablation device, comprising:
an elongate member;
a first electrode disposed along the elongate member and extending along an axis, the first electrode having a proximal end configured to couple to an energy source and a surface configured to couple to a tissue treatment region and apply ablative energy; and
a first expandable portion having a proximal end and a distal end and extending along the axis, the first expandable portion defining a first perimeter of the first electrode and having an associated first diameter with respect to the axis, wherein the first expandable portion comprises a first framework comprising a framework member, wherein the framework member comprises a helix extending along the first expandable portion, wherein a distal end of the framework member is configured to deliver electric current,
wherein the first framework is selectively expandable to transition the first expandable portion from a contracted state to an expanded state, and the first framework is selectively contractible to transition the first expandable portion from the expanded state to the contracted state,
wherein, when the first framework is expanded, the first diameter is expanded and the first expandable portion is transitioned from the contracted state to the expanded state,
wherein, when the first framework is contracted, the first diameter is contracted and the first expandable portion is transitioned from the expanded state to the contracted state, wherein a relative rotation between a proximal portion and a distal portion of the framework member transitions the first expandable portion between the contracted state and the expanded state, and wherein the relative rotation between the proximal portion and the distal portion of the framework member comprises a counter rotation of the distal portion of the framework member relative to the proximal portion of the framework member.

2. The electrical ablation device of claim 1, wherein the first electrode comprises a first flexible portion, and wherein at least a portion of the first expandable portion comprises at least a portion of the first flexible portion.

3. The electrical ablation device of claim 1, wherein the first framework is expandable to expand the first diameter to circumferentially contact a biological lumen at two or more locations about the circumference of a biological lumen.

4. The electrical ablation device of claim 1, wherein the framework member has an associated memory form and an associated retained form, and wherein the framework member is transitionable between the memory form and the retained form to expand and contract the first framework.

5. The electrical ablation device of claim 4, further comprising a retaining structure configured to retain the framework member in the retained form.

6. The electrical ablation device of claim 5, wherein the retaining structure comprises a sheath defining a channel configured to receive the framework member within a distal portion thereof, wherein the framework member is deployable from a distal end of the distal portion of the sheath, wherein the framework member is transitioned from the retained form to the memory form when deployed from the distal end of the sheath.

7. The electrical ablation device of claim 1, wherein the framework member is transitionable between an associated low temperature form and an associated high temperature form.

8. The electrical ablation device of claim 1, wherein the first framework further comprises a proximal and a distal coupler configured to couple the framework member within the first framework, wherein the proximal and distal couplers are separated by a distance, and wherein a transition from the contracted state to the expanded state further comprises a decrease in the distance between the proximal coupler and the distal coupler.

9. The electrical ablation device of claim 8, wherein the decrease in the distance between the proximal and distal coupler pivots at least a portion of the framework member outward of the axis.

10. The electrical ablation device of claim 1, further comprising:
a second electrode disposed along the elongate member and extending along the axis, the second electrode having a proximal end configured to couple to the energy source and a surface configured to couple to the tissue treatment region;
a second expandable portion having a proximal end and a distal end and extending along the axis, the second expandable portion defining a second perimeter of the second electrode having an associated second diameter with respect to the axis, wherein the second expandable portion comprises a second framework comprising one or more second framework members; and
the second framework selectively expandable to transition the second expandable portion from a contracted state to an expanded state, and the second framework selectively contractible to transition the second expandable portion from the expanded state to the contracted state, wherein, when the second framework is expanded, the second diameter is expanded and the second expandable portion is transitioned from the contracted state to the expanded state, and wherein, when the second framework is contracted, the second diameter is contracted and the second expandable portion is transitioned from the expanded state to the contracted state.

11. The electrical ablation device of claim 10, wherein the first electrode and the second electrode are separated by a distance along the elongate member, and wherein the distance between the first electrode and the second electrode is selectively adjustable.

12. A method of electrosurgically treating tissue, comprising:
obtaining the electrical ablation device of claim 1;
delivering the first electrode to a tissue treatment region comprising a biological lumen;
expanding the first electrode;
contacting the first electrode to a wall of the biological lumen proximal to the tissue to be treated; and
treating the tissue by applying, with the first electrode, one or more sequences of electric pulses to the tissue to be treated sufficient to induce cell death in the tissue by irreversible electroporation.

13. The method of electrosurgically treating tissue of claim 12, further comprising rotating the helix in a first direction within the biological lumen to continuously treat the entire biological lumen.

14. An electrical ablation device, comprising:
an elongate member;
a first electrode disposed along the elongate member and extending along an axis, the first electrode having a proximal end configured to wirelessly couple to an energy source and a surface configured to couple to a tissue treatment region and apply ablative energy; and
a first expandable portion having a proximal end and a distal end and extending along the axis, the first expandable portion defining a first perimeter of the first electrode and having an associated first diameter with respect to the axis, wherein the first expandable portion comprises a first framework comprising a framework member, wherein the framework member comprises a helix extending along the first expandable portion,
wherein a distal end of the framework member is configured to deliver electric current,
wherein the first framework is selectively expandable to transition the first expandable portion from a contracted state to an expanded state, and the first framework is selectively contractible to transition the first expandable portion from the expanded state to the contracted state,
wherein a relative rotation between a proximal portion and a distal portion of the framework member transitions the first expandable portion between the contracted state and the expanded state, and
wherein the relative rotation between the proximal portion and the distal portion of the framework member comprises a counter rotation of the distal portion of the framework member relative to the proximal portion of the framework member.

15. An electrical ablation device, comprising:
an elongate member;
an electrode disposed along the elongate member and extending along an axis, the electrode having a proximal end configured to couple to an energy source and a surface configured to couple to a tissue treatment region and apply ablative energy; and an expandable portion comprising a proximal end and a distal end and extending along the axis, the expandable portion defining a perimeter of the electrode and having an associated diameter with respect to the axis, wherein the expandable portion comprises a framework comprising a framework member, wherein the framework member comprises a helix extending along the expandable portion, wherein the framework is selectively expandable to transition the expandable portion from a contracted state to an expanded state, and the framework is selectively contractible to transition the expandable portion from the expanded state to the contracted state, wherein a relative rotation between a proximal portion and a distal portion of the framework member transitions the expandable portion between the contracted state and the expanded state, and wherein the relative rotation between the proximal portion and the distal portion of the framework member comprises a counter rotation of the distal portion of the framework member relative to the proximal portion of the framework member.

\* \* \* \* \*